United States Patent
Hoffman et al.

(10) Patent No.: US 10,467,716 B2
(45) Date of Patent: Nov. 5, 2019

(54) ATHLETIC ACTIVITY USER EXPERIENCE AND ENVIRONMENT

(71) Applicant: NIKE, Inc., Beaverton, OR (US)

(72) Inventors: Michael T. Hoffman, Portland, OR (US); Tomislav Lakovic, Portland, OR (US); Richard J. Engelberg, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 0 days.

(21) Appl. No.: 15/849,042

(22) Filed: Dec. 20, 2017

(65) Prior Publication Data

US 2018/0114287 A1 Apr. 26, 2018

Related U.S. Application Data

(63) Continuation of application No. 12/854,276, filed on Aug. 11, 2010, now Pat. No. 9,940,682.

(51) Int. Cl.
*G06Q 50/20* (2012.01)
*A63B 24/00* (2006.01)
(Continued)

(52) U.S. Cl.
CPC ......... *G06Q 50/20* (2013.01); *A63B 24/0059* (2013.01); *A63B 24/0062* (2013.01);
(Continued)

(58) Field of Classification Search
CPC ...................................................... G06Q 30/00
See application file for complete search history.

(56) References Cited

U.S. PATENT DOCUMENTS 3,797,010 A 3/1974 Adler et al.
4,371,945 A 2/1983 Karr et al.
(Continued)

FOREIGN PATENT DOCUMENTS

CN 1256752 A 6/2000
CN 1660457 A 8/2005
(Continued)

OTHER PUBLICATIONS

Jul. 23, 2006—(WO) ISR—App. No. PCT/US2005/044753.
(Continued)

*Primary Examiner* — Kira Nguyen
(74) *Attorney, Agent, or Firm* — Banner & Witcoff, Ltd.

(57) ABSTRACT

User activity including both athletic activity (e.g., running, walking, etc.) and non-athletic activity (shopping, reading articles, etc.) may be monitored and tracked by an athletic monitoring and tracking device and service. The user activity may be used to award a user with an amount of virtual currency to encourage the user to continue various activities. In one example, users may use the virtual currency to purchase or otherwise acquire various products, services, discounts and the like. A user may track an amount currency earned and/or needed relative to an amount required to acquire a desired product or service. Additionally or alternatively, a visual appearance of a user device (e.g., a watch or athletic activity band) may change based on the user's activity level, an amount of virtual currency earned and the like.

15 Claims, 21 Drawing Sheets

(51) Int. Cl.
*A63B 71/06* (2006.01)
*G06Q 10/00* (2012.01)
*G06Q 50/22* (2018.01)
*G07C 1/22* (2006.01)
*G06Q 10/06* (2012.01)
*A63B 43/00* (2006.01)
*A63B 69/00* (2006.01)
*A63B 69/06* (2006.01)
*A63B 71/12* (2006.01)
*G06F 19/00* (2018.01)
*G16H 20/30* (2018.01)

(52) U.S. Cl.
CPC ......... *A63B 71/0619* (2013.01); *G06Q 10/00* (2013.01); *G06Q 10/06* (2013.01); *G06Q 50/22* (2013.01); *G07C 1/22* (2013.01); *A63B 43/00* (2013.01); *A63B 69/0028* (2013.01); *A63B 69/06* (2013.01); *A63B 71/0616* (2013.01); *A63B 71/0622* (2013.01); *A63B 71/12* (2013.01); *A63B 2024/0065* (2013.01); *A63B 2024/0068* (2013.01); *A63B 2024/0071* (2013.01); *A63B 2071/063* (2013.01); *A63B 2071/0625* (2013.01); *A63B 2071/0641* (2013.01); *A63B 2071/0663* (2013.01); *A63B 2220/12* (2013.01); *A63B 2220/17* (2013.01); *A63B 2220/20* (2013.01); *A63B 2220/30* (2013.01); *A63B 2220/40* (2013.01); *A63B 2220/53* (2013.01); *A63B 2220/806* (2013.01); *A63B 2220/833* (2013.01); *A63B 2220/836* (2013.01); *A63B 2225/20* (2013.01); *A63B 2225/50* (2013.01); *A63B 2225/54* (2013.01); *A63B 2230/04* (2013.01); *A63B 2230/06* (2013.01); *A63B 2230/207* (2013.01); *A63B 2230/75* (2013.01); *A63B 2243/007* (2013.01); *A63B 2243/0025* (2013.01); *A63B 2243/0037* (2013.01); *A63B 2244/09* (2013.01); *A63B 2244/18* (2013.01); *A63B 2244/19* (2013.01); *A63B 2244/20* (2013.01); *G06F 19/3481* (2013.01); *G16H 20/30* (2018.01)

(56) References Cited

U.S. PATENT DOCUMENTS

| | | | |
|---|---|---|---|
| 4,571,680 A | 2/1986 | Wu | |
| 4,578,769 A | 3/1986 | Frederick | |
| 4,674,743 A | 6/1987 | Hirano | |
| 4,703,445 A | 10/1987 | Dassler | |
| 4,736,312 A | 4/1988 | Dassler et al. | |
| 4,763,284 A | 8/1988 | Carlin | |
| 4,771,394 A | 9/1988 | Cavanagh | |
| 4,828,257 A | 5/1989 | Dyer et al. | |
| 4,962,469 A | 10/1990 | Ono et al. | |
| 5,033,013 A | 7/1991 | Kato et al. | |
| 5,335,188 A | 8/1994 | Brisson | |
| 5,373,651 A | 12/1994 | Wood | |
| 5,485,402 A | 1/1996 | Smith et al. | |
| 5,500,635 A | 3/1996 | Mott | |
| 5,524,637 A | 6/1996 | Erickson | |
| 5,553,007 A | 9/1996 | Brisson | |
| 5,583,776 A | 12/1996 | Levi et al. | |
| 5,596,652 A | 1/1997 | Piatek et al. | |
| 5,598,849 A | 2/1997 | Browne | |
| 5,678,448 A | 10/1997 | Fullen et al. | |
| 5,720,200 A | 2/1998 | Anderson et al. | |
| 5,724,265 A | 3/1998 | Hutchings | |
| 5,749,372 A | 5/1998 | Allen et al. | |
| 5,793,882 A | 8/1998 | Piatek et al. | |
| 5,802,492 A | 9/1998 | DeLorme et al. | |
| 5,815,954 A | 10/1998 | Huang | |
| 5,857,066 A | 1/1999 | Wyche et al. | |
| 5,857,939 A | 1/1999 | Kaufman | |
| 5,875,571 A | 3/1999 | Huang | |
| 5,890,997 A | 4/1999 | Roth | |
| 5,931,763 A | 8/1999 | Alessandri | |
| 5,955,667 A | 9/1999 | Fyfe | |
| 6,002,982 A | 12/1999 | Fry | |
| 6,013,007 A | 1/2000 | Root et al. | |
| 6,018,705 A | 1/2000 | Gaudet et al. | |
| 6,052,654 A | 4/2000 | Gaudet et al. | |
| 6,072,467 A | 6/2000 | Walker | |
| 6,077,193 A | 6/2000 | Buhler et al. | |
| 6,122,960 A | 9/2000 | Hutchings et al. | |
| 6,132,391 A | 10/2000 | Onari et al. | |
| 6,183,425 B1 | 2/2001 | Whalen et al. | |
| 6,198,431 B1 | 3/2001 | Gibson | |
| 6,285,314 B1 | 9/2001 | Nagatsuma et al. | |
| 6,312,363 B1 | 11/2001 | Watterson et al. | |
| 6,356,856 B1 | 3/2002 | Damen et al. | |
| 6,375,612 B1 | 4/2002 | Guichon et al. | |
| 6,396,413 B2 | 5/2002 | Hines et al. | |
| 6,424,264 B1 | 7/2002 | Giraldin et al. | |
| 6,430,843 B1 | 8/2002 | Potter et al. | |
| 6,447,424 B1 | 9/2002 | Ashby et al. | |
| 6,456,930 B1 | 9/2002 | Naito et al. | |
| 6,463,385 B1 | 10/2002 | Fry | |
| 6,493,652 B1 | 12/2002 | Ohlenbusch et al. | |
| 6,498,994 B2 | 12/2002 | Vock et al. | |
| 6,513,381 B2 | 2/2003 | Fyfe et al. | |
| 6,522,266 B1 | 2/2003 | Soehren et al. | |
| 6,526,158 B1 | 2/2003 | Goldberg | |
| 6,531,963 B1 | 3/2003 | Nyfelt | |
| 6,539,336 B1 | 3/2003 | Vock et al. | |
| 6,545,661 B1 | 4/2003 | Goschy et al. | |
| 6,549,845 B2 | 4/2003 | Eakle, Jr. et al. | |
| 6,569,092 B1 | 5/2003 | Guichon et al. | |
| 6,571,193 B1 | 5/2003 | Unuma et al. | |
| 6,582,342 B2 | 6/2003 | Kaufman | |
| 6,600,407 B2 | 7/2003 | Paek | |
| 6,614,352 B2 | 9/2003 | Pellet et al. | |
| 6,614,392 B2 | 9/2003 | Howard | |
| 6,623,427 B2 | 9/2003 | Mandigo | |
| 6,626,799 B2 | 9/2003 | Watterson et al. | |
| 6,716,139 B1 | 4/2004 | Hosseinzadeh-Dolkhani et al. | |
| 6,735,542 B1 | 5/2004 | Burgett et al. | |
| 6,788,200 B1 | 9/2004 | Jamel et al. | |
| 6,805,006 B2 | 10/2004 | Guzman | |
| 6,813,582 B2 | 11/2004 | Levi et al. | |
| 6,817,979 B2 | 11/2004 | Nihtila | |
| 6,865,825 B2 | 3/2005 | Bailey, Sr. et al. | |
| 6,876,947 B1 | 4/2005 | Darley et al. | |
| 6,882,955 B1 | 4/2005 | Ohlenbusch et al. | |
| 6,898,550 B1 | 5/2005 | Blackadar et al. | |
| 6,997,852 B2 | 2/2006 | Watterson et al. | |
| 7,003,122 B2 | 2/2006 | Chen | |
| 7,028,547 B2 | 4/2006 | Shiratori et al. | |
| 7,062,225 B2 | 6/2006 | White | |
| 7,174,277 B2 | 2/2007 | Vock et al. | |
| 7,251,454 B2 | 7/2007 | White | |
| 7,254,516 B2 | 8/2007 | Case, Jr. et al. | |
| 7,519,327 B2 | 4/2009 | White | |
| 7,603,255 B2 | 10/2009 | Case, Jr. et al. | |
| 7,979,899 B2 * | 7/2011 | Guo | H04L 63/0823 726/20 |
| 2001/0054014 A1 | 12/2001 | Noda et al. | |
| 2002/0019296 A1 | 2/2002 | Freeman et al. | |
| 2002/0022551 A1 | 2/2002 | Watterson et al. | |
| 2002/0027524 A1 | 3/2002 | Pippin | |
| 2002/0077883 A1 | 6/2002 | Lancos et al. | |
| 2002/0080198 A1 | 6/2002 | Giraldin et al. | |
| 2002/0091796 A1 | 7/2002 | Higginson et al. | |
| 2002/0142887 A1 | 10/2002 | O'Malley | |
| 2002/0147629 A1 | 10/2002 | Alsafadi et al. | |
| 2002/0147642 A1 | 10/2002 | Avallone et al. | |
| 2002/0156677 A1 | 10/2002 | Peters et al. | |
| 2002/0165758 A1 | 11/2002 | Hind et al. | |
| 2002/0173407 A1 | 11/2002 | Bowman | |
| 2002/0174025 A1 | 11/2002 | Hind et al. | |
| 2003/0009308 A1 | 1/2003 | Kirtley | |

(56) References Cited

U.S. PATENT DOCUMENTS

| | | |
|---|---|---|
| 2003/0009382 A1 | 1/2003 | D'Arbeloff et al. |
| 2003/0009913 A1 | 1/2003 | Potter et al. |
| 2003/0040922 A1 | 2/2003 | Bodin |
| 2003/0069108 A1 | 4/2003 | Kaiserman et al. |
| 2003/0090386 A1 | 5/2003 | Giraldin et al. |
| 2003/0093248 A1 | 5/2003 | Vock et al. |
| 2003/0114984 A1 | 6/2003 | Scherzinger |
| 2003/0160732 A1 | 8/2003 | Van Heerden et al. |
| 2003/0163283 A1 | 8/2003 | O'Brien |
| 2003/0163287 A1 | 8/2003 | Vock et al. |
| 2003/0171189 A1 | 9/2003 | Kaufman |
| 2004/0046692 A1 | 3/2004 | Robson et al. |
| 2004/0094613 A1 | 5/2004 | Shiratori et al. |
| 2004/0102931 A1 | 5/2004 | Ellis et al. |
| 2004/0177531 A1 | 9/2004 | DiBenedetto et al. |
| 2004/0209600 A1 | 10/2004 | Werner et al. |
| 2004/0224718 A1 | 11/2004 | Chen |
| 2004/0246145 A1 | 12/2004 | Andrews et al. |
| 2005/0033515 A1 | 2/2005 | Bozzone |
| 2005/0171410 A1 | 8/2005 | Hjelt et al. |
| 2005/0184878 A1 | 8/2005 | Grold et al. |
| 2005/0209050 A1 | 9/2005 | Bartels |
| 2005/0233859 A1 | 10/2005 | Takai et al. |
| 2005/0248718 A1 | 11/2005 | Howell et al. |
| 2005/0261609 A1 | 11/2005 | Collings et al. |
| 2006/0013351 A1 | 1/2006 | Crider |
| 2006/0084551 A1 | 4/2006 | Volpe |
| 2006/0099556 A1 | 5/2006 | Yeo et al. |
| 2006/0189437 A1 | 8/2006 | Cohen et al. |
| 2006/0204045 A1 | 9/2006 | Antonucci |
| 2007/0016444 A1* | 1/2007 | Holkkola ............... G06Q 50/22 705/2 |
| 2007/0247306 A1* | 10/2007 | Case, Jr. .............. A43B 3/0005 340/539.11 |
| 2008/0077489 A1 | 3/2008 | Gilley et al. |
| 2009/0144639 A1 | 6/2009 | Nims |
| 2009/0149299 A1* | 6/2009 | Tchao ................. G06F 19/3481 482/9 |
| 2009/0164219 A1 | 6/2009 | Yeung et al. |
| 2009/0262088 A1 | 10/2009 | Moll-Carrillo et al. |
| 2010/0069148 A1 | 3/2010 | Cargill |
| 2011/0059769 A1 | 3/2011 | Brunolli |

FOREIGN PATENT DOCUMENTS

| | | |
|---|---|---|
| DE | 19860603 A1 | 7/1999 |
| DE | 202004013989 U1 | 11/2004 |
| EP | 1134555 A1 | 9/2001 |
| FR | 2754723 A1 | 4/1998 |
| GB | 2352348 A | 1/2001 |
| JP | 08068846 | 12/1996 |
| JP | 09089584 | 4/1997 |
| JP | H09-198473 A | 7/1997 |
| JP | 2001257746 A | 9/2001 |
| JP | 2001-344424 A | 12/2001 |
| JP | 2002022479 A | 1/2002 |
| JP | 2002024404 A | 1/2002 |
| JP | 2002264879 A | 9/2002 |
| JP | 2002310679 A | 10/2002 |
| JP | 2002331058 A | 11/2002 |
| JP | 2002357438 A | 12/2002 |
| JP | 2003067132 A | 3/2003 |
| JP | 2003123192 A | 4/2003 |
| JP | 2003141260 A | 5/2003 |
| JP | 2003168194 A | 6/2003 |
| JP | 2003316905 A | 11/2003 |
| JP | 2003331063 A | 11/2003 |
| JP | 2004037413 A | 2/2004 |
| JP | 2004085301 A | 3/2004 |
| JP | 2004085511 A | 3/2004 |
| JP | 2004118410 A | 4/2004 |
| JP | 2004138474 A | 5/2004 |
| JP | 2004233058 A | 8/2004 |
| JP | 2004350947 A | 12/2004 |
| JP | 2008083776 A | 4/2008 |
| JP | 2009247836 A | 10/2009 |
| WO | 200033031 A1 | 6/2000 |
| WO | 0142809 A2 | 6/2001 |
| WO | 0188477 A2 | 11/2001 |
| WO | 02055959 A1 | 7/2002 |
| WO | 02055960 A1 | 7/2002 |
| WO | 2005017459 A1 | 2/2005 |
| WO | 2009073607 A2 | 6/2009 |

OTHER PUBLICATIONS

May 17, 2011—(EP) Extended European Search Report—App. No. 11155502.5.

May 11, 2011—(EP) Extended European Search Report—App. No. 11155505.8.

May 17, 2011—(EP) Extended European Search Report—App. No. 11155506.6.

May 18, 2011—(EP) Extended European Search Report—App. No. 11155507.4.

May 18, 2011—(EP) Extended European Search Report—App. No. 11155508.2.

May 19, 2011—(EP) Extended European Search Report—App. No. 11155509.0.

Mar. 31, 2016—(EP) Extended Search Report—App. 11746106.1.

* cited by examiner

ATHLETIC ACTIVITY USER EXPERIENCE AND ENVIRONMENT

CROSS-REFERENCE TO RELATED APPLICATION

This application is a continuation of and claims priority to U.S. patent application Ser. No. 12/854,276, filed Aug. 11, 2010, which is expressly incorporated herein by reference in its entirety for any and all non-limiting purposes.

BACKGROUND

While most people appreciate the importance of physical fitness, many have difficulty finding the motivation required to maintain a regular exercise program. Some people find it particularly difficult to maintain an exercise regimen that involves continuously repetitive motions, such as running, walking and bicycling.

Experienced athletes and trainers have found that feedback provides many people with motivation to maintain a regular exercise program. When a person can directly experience the results provided by an exercise program, that person typically will be encouraged to continue exercising.

Additionally, individuals may view exercise as work or a chore and thus, separate it from enjoyable aspects of their daily lives. This clear separation between athletic activity and other activities reduces the amount of motivation that an individual might have toward exercising. Athletic activity services and systems directed toward encouraging individuals to engage in athletic activities might also be too focused on one or more particular activities while an individual's interest are ignored. This may further decrease a user's interest in participating in athletic activities or using the athletic activity services and systems.

BRIEF SUMMARY

According to one or more aspects, an activity monitoring environment and system may be used to encourage individuals to participate in athletic activities and improve their fitness levels. The activity monitoring environment and system may merge athletic activity and non-athletic activity into a single ecosystem to garner enhanced user interest by providing incentives and motivation to engage in athletic activities. For example, an individual's personal site on an activity tracking and monitoring service may be customized according to the interests of the individual as determined based on their behavior, their purchases, their athletic activity and/or combinations thereof. Accordingly, when an individual views his or her activity site, the individual may feel more engaged because relevant and interesting information is presented therein. Additionally or alternatively, an activity monitoring system may include other engines such as analytical engines and marketing engines to customize navigation through and content included in a web site according to an individual's preferences. Further, events may be customized and automatically generated based on an analysis of events in which an individual has participated in the past and/or their results therein.

The activity monitoring services and systems may further motivate a user to exercise by rewarding the users with activity points when the user performs a variety of different athletic and non-athletic activities. Activity points may comprise a form of currency that may be spent on various rewards. For example, activity points may be used to purchase products, services, discounts, status upgrades and the like. In one or more arrangements, activity points may be categorized or awarded in different grades. For example, activity points of a first grade may more valuable than activity points of a second grade. Different grades may be used when activity points are earned through different sources, through different activities and/or using different devices such as certified devices versus non-certified devices or manual activity information entry. The disparity between such submission methods may correspond to the difference in perceived reliability (or lack thereof) of the information source. Activity points may be converted into activity points of other grades based on a specified conversion rate. Furthermore, in some arrangements, activity points of different grades may be displayed differently in a user interface, e.g., in different colors, using different gages/representations, with different labels and/or combinations thereof.

In examples where activity points are earned through non-athletic activity such as shopping, a system may award activity points for each dollar spent shopping at sponsoring companies. Accordingly, a user may be encouraged to accumulate activity points in multiple ways because the points may be earned through both athletic and non-athletic activities. In some arrangements, a limit may be defined for an amount of activity points that may be earned for different types of activity. For example, a system may limit the number of activity points that may be earned through non-athletic activities to 500 points per day and the number of activity points earned through athletic activities to 750 points per day.

According to another aspect, various conversion rates may be defined and used for converting a non-point activity metric into activity points. Different activities may be worth different levels of activity points. For example, shopping may accumulate activity points at a slower rate (e.g., points/dollar) than performing athletic activities. Conversion rates may also depend on the type of devices used to monitor or collect the activity information to be converted. Other factors that may be considered in determining a conversion rate may include, for example, a user's athletic characteristics (e.g., resting heart rate, previous workout, best workout, preferred athletic activities) and non-athletic characteristics (e.g., income, age, gender, etc.).

Achievements may also be sources of activity points. For example, if a user reaches a milestone or accomplishes some other type of achievement, a number of activity points may be awarded to the user. In other arrangements, the user may be challenged by one or more other users and a winner may be awarded a certain number of activity points. Participation in events and viewing advertisements may be additional sources of activity points.

Activity points may be consumed in various manners. As noted, activity points may be spent on rewards. In another example, activity points may be donated, e.g., to charitable organizations or gifted to others. In yet another example, activity points may be sold. Limits may be placed the various types of activity point consumption.

These and other features of the invention will become apparent from the following detailed description.

DETAILED DESCRIPTION

Athletic Activity Overview

Figure 1:
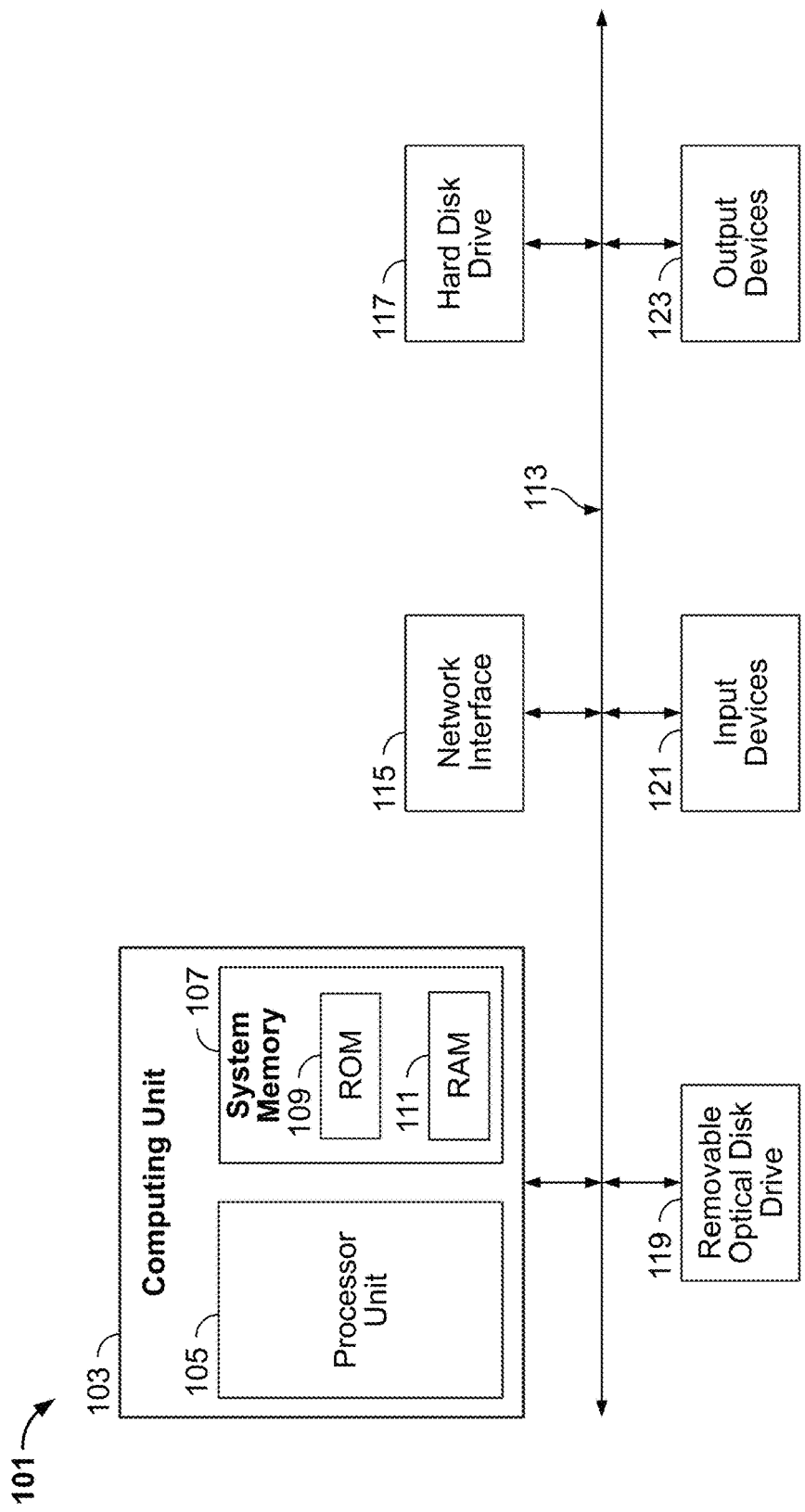
FIG. 1 illustrates a computing device that may be used to implement various examples of the invention.

Aspects of the invention relate to the measurement, collection, display and management of athletic and non-athletic information. As will be appreciated by those of ordinary skill in the art, athletic information must first be obtained from an individual person. With various implementations of the invention, one or more different athletic information monitoring devices may be used to measure and record athletic data corresponding to athletic activity performed by a person and to convert that information into a form of currency. Typically, an athletic information monitoring device will incorporate a sensor for measuring parameters relating to the person being monitored, and a computing device for processing the parameters measured by the sensor.

Once an athletic information monitoring device has recorded athletic information for a person's athletic activity, the person may then transfer the recorded athletic information to one or more separate devices, in order to view the recorded athletic data. A user may, for example, download the recorded athletic information from an athletic information monitoring device to a separate collection device. The collection device may, in turn, transfer the athletic information collected from the athletic information monitoring device to a separate display configuration device, where the athletic information can be organized and configured for subsequent viewing with, e.g., still another device. As will be discussed in more detail below, various implementations of the invention will allow a person to record, collect and display athletic information using a group of computing devices communicating over a network, such as the Internet.

For example, some aspects described herein allow a person to measure and record athletic information using a special-purpose computing device. The user can then transfer the recorded athletic information to a local computing device, such as a personal desktop or laptop computer. More particularly, a user can download recorded athletic information from the athletic information monitoring device to a collection software tool on a local computer that acts as a "client" in a computer network. The collection software tool will then transfer the downloaded athletic information through the network to a remote "server" computer. A display configuration software tool on the remote server computer will then save the transferred athletic information. Later, a person can use the client computer or another local computer to retrieve the stored athletic information from the server computer. In response to a display request from a local computer, the display configuration software tool will configure the requested athletic information for display on the local computer, and then transmit the configured athletic information to the local computer for display.

Computing Device

Various examples of the invention may be implemented using electronic circuitry configured to perform one or more functions. For example, with some embodiments of the invention, the athletic information monitoring device, the collection device, the display device or any combination thereof may be implemented using one or more application-specific integrated circuits (ASICs). More typically, however, components of various examples of the invention will be implemented using a programmable computing device executing firmware or software instructions, or by some combination of purpose-specific electronic circuitry and firmware or software instructions executing on a programmable computing device.

Accordingly, FIG. 1 shows one illustrative example of a computer 101 that can be used to implement various embodiments of the invention. As seen in this figure, the computer 101 has a computing unit 103. The computing unit 103 typically includes a processing unit 105 and a system memory 107. The processing unit 105 may be any type of processing device for executing software instructions, but will conventionally be a microprocessor device. The system memory 107 may include both a read-only memory (ROM) 109 and a random access memory (RAM) 111. As will be appreciated by those of ordinary skill in the art, both the read-only memory (ROM) 109 and the random access memory (RAM) 111 may store software instructions for execution by the processing unit 105.

The processing unit 105 and the system memory 107 are connected, either directly or indirectly, through a bus 113 or alternate communication structure to one or more peripheral devices. For example, the processing unit 105 or the system memory 107 may be directly or indirectly connected to additional memory storage, such as the hard disk drive 115, the removable magnetic disk drive 117, the optical disk drive 119, and the flash memory card 121. The processing unit 105 and the system memory 107 also may be directly or indirectly connected to one or more input devices 123 and one or more output devices 125. The input devices 123 may include, for example, a keyboard, touch screen, a remote control pad, a pointing device (such as a mouse, touchpad, stylus, trackball, or joystick), a scanner, a camera or a microphone. The output devices 125 may include, for example, a monitor display, television, printer, stereo, or speakers.

Still further, the computing unit 103 will be directly or indirectly connected to one or more network interfaces 127 for communicating with a network. This type of network interface 127, also sometimes referred to as a network adapter or network interface card (NIC), translates data and control signals from the computing unit 103 into network messages according to one or more communication protocols, such as the Transmission Control Protocol (TCP), the Internet Protocol (IP), and the User Datagram Protocol (UDP). These protocols are well known in the art, and thus will not be discussed here in more detail. An interface 127 may employ any suitable connection agent for connecting to a network, including, for example, a wireless transceiver, a power line adapter, a modem, or an Ethernet connection.

It should be appreciated that, in addition to the input, output and storage peripheral devices specifically listed above, the computing device may be connected to a variety of other peripheral devices, including some that may perform input, output and storage functions, or some combination thereof. For example, the computer 101 may be connected to a digital music player, such as an IPOD® brand digital music player available from Apple, Inc. of Cupertino, Calif. As known in the art, this type of digital music player can serve as both an output device for a computer (e.g., outputting music from a sound file or pictures from an image file) and a storage device. In addition, this type of digital music player also can serve as an input device for inputting recorded athletic information, as will be discussed in more detail below.

In addition to a digital music player, the computer 101 may be connected to or otherwise include one or more other peripheral devices, such as a telephone. The telephone may be, for example, a wireless "smart phone." As known in the art, this type of telephone communicates through a wireless network using radio frequency transmissions. In addition to simple communication functionality, a "smart phone" may also provide a user with one or more data management functions, such as sending, receiving and viewing electronic messages (e.g., electronic mail messages, SMS text messages, etc.), recording or playing back sound files, recording or playing back image files (e.g., still picture or moving video image files), viewing and editing files with text (e.g., Microsoft Word or Excel files, or Adobe Acrobat files), etc. Because of the data management capability of this type of telephone, a user may connect the telephone with the computer 101 so that their data may be maintained and synchronized.

Of course, still other peripheral devices may be included with or otherwise connected to a computer 101 of the type illustrated in FIG. 1, as is well known in the art. In some cases, a peripheral device may be permanently or semi-permanently connected to the computing unit 103. For example, with many computers, the computing unit 103, the hard disk drive 117, the removable optical disk drive 119 and a display are semi-permanently encased in a single housing. Still other peripheral devices may be removably connected to the computer 101. The computer 101 may include, for example, one or more communication ports through which a peripheral device can be connected to the computing unit 103 (either directly or indirectly through the bus 113). These communication ports may thus include a parallel bus port or a serial bus port, such as a serial bus port using the Universal Serial Bus (USB) standard or the IEEE 1394 High Speed Serial Bus standard (e.g., a Firewire port). Alternately or additionally, the computer 101 may include a wireless data "port," such as a Bluetooth interface, a Wi-Fi interface, an infrared data port, or the like.

It should be appreciated that a computing device employed according various examples of the invention may include more components than the computer 101 illustrated in FIG. 1, fewer components than the computer 101, or a different combination of components than the computer 101. Some implementations of the invention, for example, may employ one or more computing devices that are intended to have a very specific functionality, such as a digital music player or server computer. These computing devices may thus omit unnecessary peripherals, such as the network interface 115, removable optical disk drive 119, printers, scanners, external hard drives, etc. Some implementations of the invention may alternately or additionally employ computing devices that are intended to be capable of a wide variety of functions, such as a desktop or laptop personal computer. These computing devices may have any combination of peripheral devices or additional components as desired.

Athletic Information Monitoring Device

Figure 2:
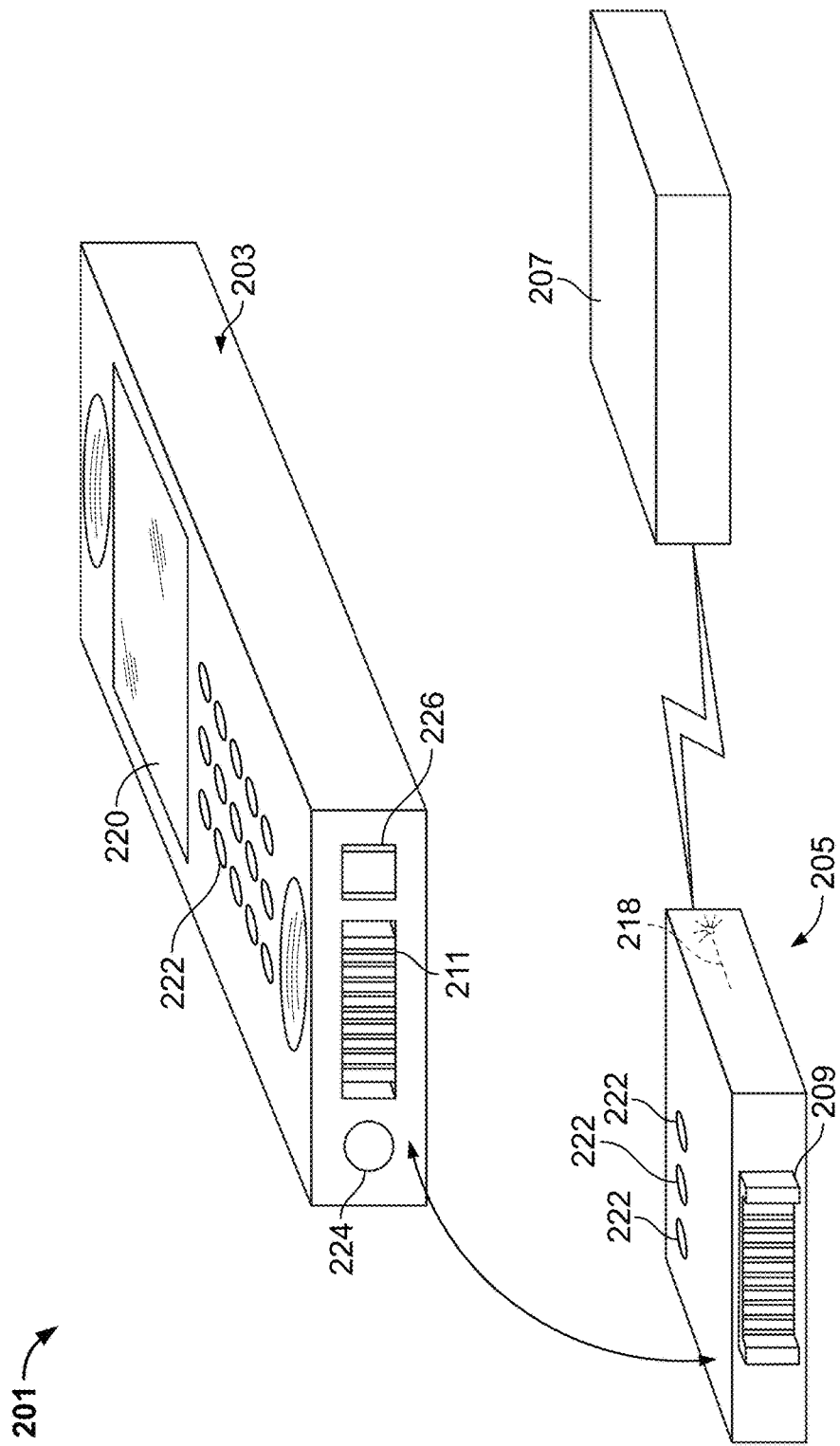
FIGS. 2 and 3 illustrate an example of an athletic information monitoring device that may be employed according to various examples of the invention.

FIG. 2 illustrates one example of an athletic information monitoring device 201 that may be employed according to various examples of the invention to measure athletic information corresponding a user's athletic activity. As shown in this figure, the athletic information monitoring device 201 includes a digital music player 203, an electronic interface device 205, and an athletic parameter measurement device 207. As will be described in more detail, the digital music player 203 is (releasably) connected to the electronic interface device 205, and the combination is worn or otherwise carried by the user while he or she is performing an athletic activity, such as running or walking. The athletic parameter measurement device 207 also is worn or carried by the user while he or she is performing an athletic activity, and it measures one or more athletic parameters relating to the athletic performance being performed by the user. The athletic parameter measurement device 207 transmits signals to the electronic interface device 205 that correspond to the measured athletic parameter. The electronic interface device 205 receives the signals from the athletic parameter measurement device 207 and provides the received information to the digital music player 203 (optionally, after data processing within the interface device 205).

Figure 3:
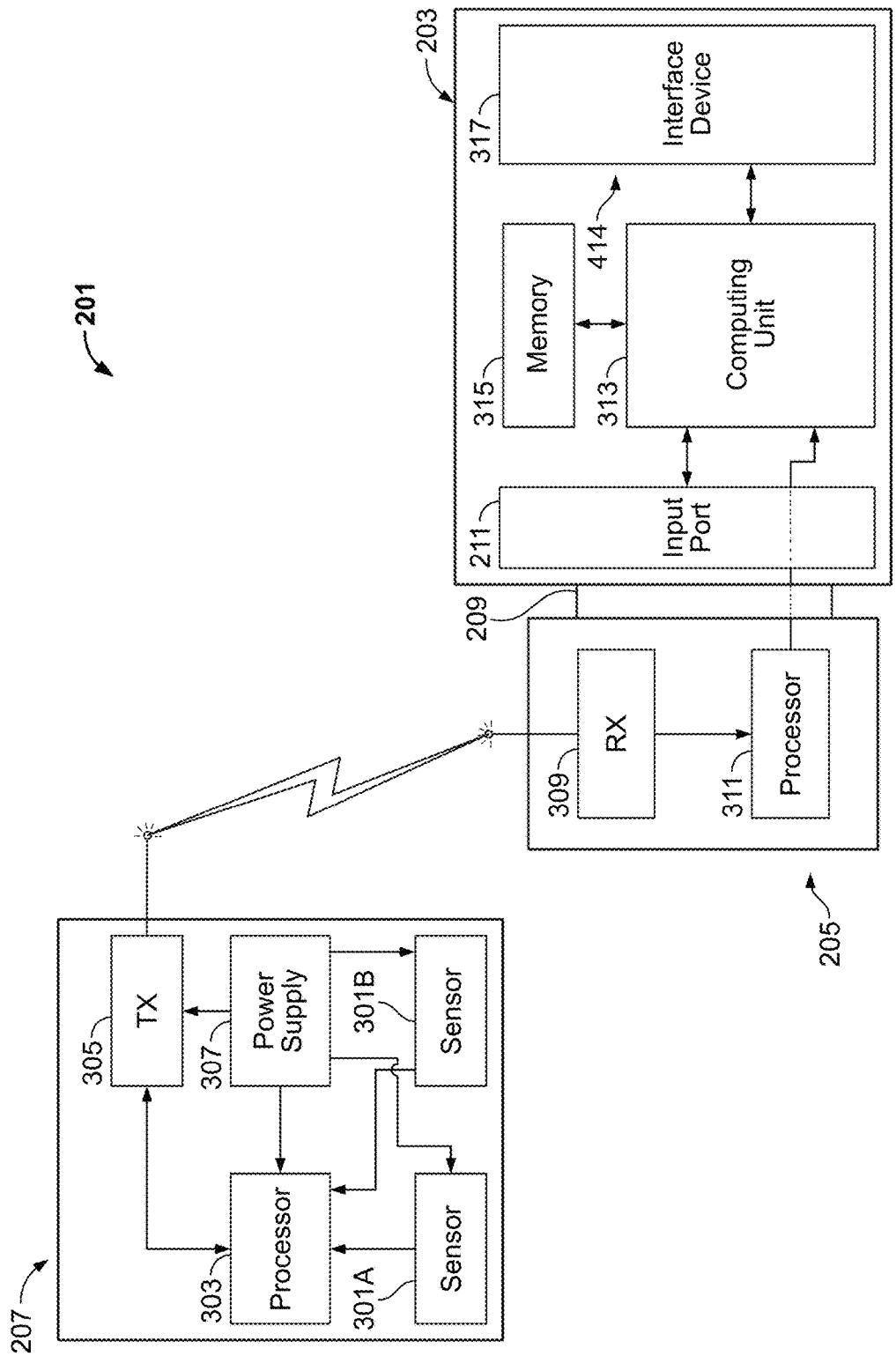
Figure 4:
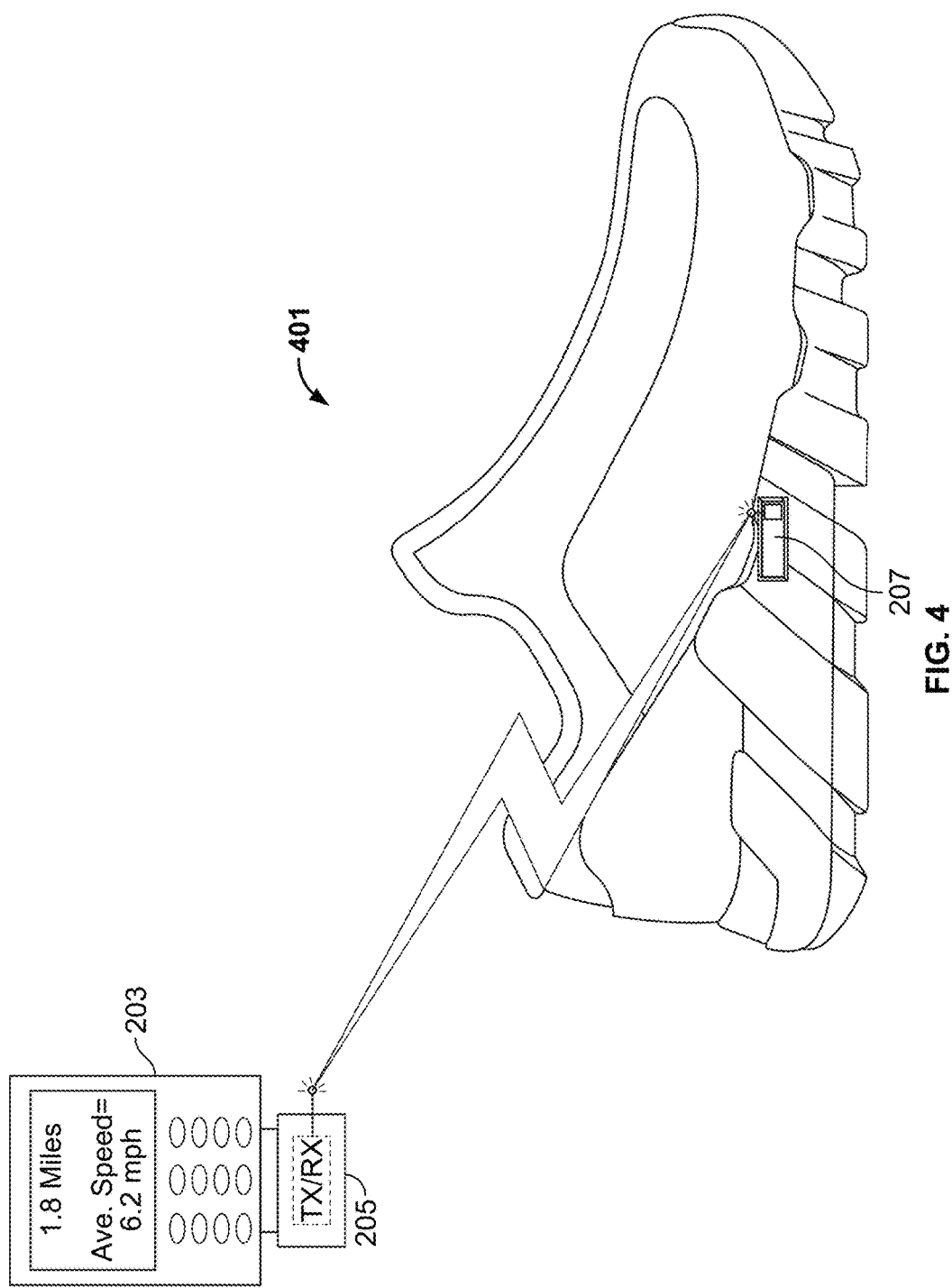
FIG. 4 illustrates one environment in which an athletic parameter measurement device according to various examples of the invention may be employed.

As shown in more detail in FIG. 3, the athletic parameter measurement device 207 includes one or more sensors 301 for measuring an athletic parameter associated with a person wearing or otherwise using the athletic parameter measurement device 207. With the illustrated implementations, for example, the sensors 301A and 301B may be accelerometers (such as piezoelectric accelerometers) for measuring the acceleration of the athletic parameter measurement device 207 in two orthogonal directions. The athletic parameter measurement device 207 is carried or otherwise worn by a user to measure the desired athletic parameter while the user exercises. For example, as shown in FIG. 4, the athletic parameter measurement device 207 may be located the sole of a user's shoe 401 while the user walks or runs. With this arrangement, the sensors 301 will produce electrical signals corresponding to the movement of the user's foot. As known in the art, these signals can then be used to generate athletic data representative of the athletic activity performed by the user (e.g., the speed and/or distance moved by the user).

The athletic parameter measurement device 207 also includes a processor 303 for processing the electrical signals output by the sensors 301. With some implementations of the invention, the processor 303 may be a programmable microprocessor. For still other implementations of the invention, however, the processor 303 may be a purpose-specific circuit device, such as an ASIC. The processor 303 may perform any desired operation on the signals output from the sensors 301, such as curve smoothing, noise filtering, outlier removal, amplification, summation, integration, or the like. The processor 303 provides the processed signals to a transmitter 305. The athletic parameter measurement device 207 also includes a power supply 307, for providing power to the sensors 301, the processor 303, and the transmitter 305 as needed. The power supply 307 may be, for example, a battery.

The athletic parameter measurement device 207 transmits the processed signals to the electronic interface device 205, as seen in FIG. 4. Returning now to FIG. 3, the electronic interface device 205 includes a receiver 309 which receives the processed signals transmitted by the transmitter 305 in the athletic parameter measurement device 207. The receiver 309 relays the processed signals to a second processor 311, which processes the signals further. Like the processor 303, the processor 311 may perform any desired operation on the processed signals, such as curve smoothing, noise filtering, outlier removal, amplification, summation, integration, or the like. Alternatively, if desired, the interface device 205 may simply pass the signals from the transmitter 305 to the player 203 without any further processing The processor 303 provides the processed signals to the digital music player 203. Referring back now to FIG. 2, the electronic interface device 205 includes a connector system 209 that physically plugs into and connects with a conventional input port 211 provided on digital music player 203. The input port 211 into which the connector system 209 of the electronic interface device 205 connects may be any desired type of input port for transferring data, such as a parallel data port, a serial data port, an earphone or microphone jack, etc. The connector system 209 may include any suitable connecting devices, such as wires, pins, electrical connectors, and the like, so as to make an electrical connection or other suitable connection with corresponding elements provided in the input port 211 of the digital music player 203 (e.g., to allow electronic and/or data communications between the interface device 205 and the digital music player 203). If necessary or desired, additional securing elements may be provided to securely connect the interface device 205 to the digital music player 203, such as straps, hooks, buckles, clips, clamps, clasps, retaining elements, mechanical connectors, and the like.

Returning now to FIG. 3, the processor 311 provides the processed signals to the computing unit 313 of the digital music player 203. The computing unit 313 may initially store the processed signals in the memory 315. Further, with some implementations of the invention, the computing unit 313 may operate on the processed signals provided by the athletic information monitoring device 201 to generate a "real-time" set of athletic data corresponding to the athletic activity performed by the user. For example, if the athletic information monitoring device 201 includes accelerometers for measuring the movement of the user's foot, the computing unit 313 may analyze the processed signals from the athletic information monitoring device 201 to generate a set of athletic data describing the user's speed at specific instances during the user's athletic activity and the total distance traveled by the user at each of those specific instances. Various techniques for determining a user's speed from accelerometer signals are described in, for example, U.S. Pat. No. 6,898,550 to Blackadar et al., entitled "Monitoring Activity Of A User In Locomotion On Foot," and issued on May 24, 2005, U.S. Pat. No. 6,882,955 to Ohlenbusch et al., entitled "Monitoring Activity Of A User In Locomotion On Foot," and issued on Apr. 19, 2005, U.S. Pat. No. 6,876,947 to Darley et al., entitled "Monitoring Activity Of A User In Locomotion On Foot," and issued on Apr. 5, 2005, U.S. Pat. No. 6,493,652 to Ohlenbusch et al., entitled "Monitoring Activity Of A User In Locomotion On Foot," and issued on Dec. 10, 2002, U.S. Pat. No. 6,298,314 to Blackadar et al., entitled "Detecting The Starting And Stopping Of Movement Of A Person On Foot," and issued on Oct. 2, 2001, U.S. Pat. No. 6,052,654 to Gaudet et al., entitled "Measuring Foot Contact Time And Foot Loft Time Of A Person In Locomotion," and issued on Apr. 18, 2000, U.S. Pat. No. 6,018,705 to Gaudet et al., entitled "Measuring Foot Contact Time And Foot Loft Time Of A Person In Locomotion," and issued on Jan. 25, 2000, each of which is incorporated entirely herein by reference.

The athletic data set may also include a time value associated with each speed value and/or each distance value. If the athletic information monitoring device 201 can be employed to collect athletic information from different users, then the athletic data computing unit 313 may additionally prompt the user to identify himself or herself in some way. This identification information may then be included with the athletic data set generated from the information provided by the athletic information monitoring device 201. Once the computing unit 313 has generated a set of athletic data from the information provided by the athletic information monitoring device 201, the computing unit 313 may store the athletic data set in the memory 315. As will be discussed in more detail below, when the digital music player 203 subsequently is connected to a computing device implementing an athletic information collection tool, the computing unit 313 will download the athletic data to a display configuration tool hosted on a remote computing device.

While wireless communication between the athletic parameter measurement device 207 and the interface device 205 is described for the embodiments illustrated in FIGS. 2-4, any desired manner of communicating between the athletic parameter measurement device 207 and the interface device 205 may be used without departing from the invention, including wired connections. Also, any desired way of placing data derived from the physical or physiological data from the athletic parameter measurement device 207 in the proper form or format for display on or output from electronic device 203 may be provided without departing from the invention. For example, if desired, the athletic parameter measurement device 207 may be specially designed and/or programmed for use with one or more specific electronic devices, e.g., pre-programmed and/or wired to operate with a specific device or devices and to provide output data in a form and format suitable for those devices. In this situation, the interface devices 205 may be marketed and sold to specifically target certain electronic devices, such as specific models of digital music players and even other electronic devices, such as telephones, watches, personal digital assistants, etc. As another alternative, if desired, the interface devices 205 may be programmed at a later time to operate with a wide variety of different electronic devices, e.g., by downloading display or device driver and/or format data for specific electronic devices from the Internet, from disk, or from another source, etc.

If desired, in accordance with at least some examples of this invention, the electronic interface device 205 and/or electronic player device 203 may further include a display 220 and/or a user input system 222, such as one or more rotary input devices, switches, buttons (as shown in the illustrated example in FIG. 2), mouse or trackball elements, touch screens, or the like, or some combination thereof. The display 220 may be employed to show, for example, information relating to music being played by the digital music player 203, information relating to the athletic information signals being received by the digital music player 203, athletic data being generated by the digital music player 203 from the received athletic information signals, etc. The user input system 222 may be employed, for example: to control one or more aspects of the processing of the input data received via interface device 205, to control input data receipt (e.g., timing, types of information received, on-demand data requests, etc.), to control data output to or by the electronic device 203, to control the athletic parameter measurement device 207, etc. Alternatively or additionally, if desired, the input system on the digital music player 203 (e.g., buttons 222, a touch screen, a digitizer/stylus based input, a rotary input device, a trackball or roller ball, a mouse, etc.), may be used to provide user input data to the interface device 205 and/or to the athletic parameter measurement device 207. As still another example, if desired, a voice input system may be provided with the interface device 205 and/or the digital music player 203, e.g., to enable user input via voice commands. Any other desired type of user input system, for control of any system elements and/or for any purpose, may be provided without departing from the invention.

The digital music player 203 may include additional input and/or output elements, e.g., such as ports 224 and 226 shown in FIG. 2, e.g., for headphones (or other audio output), power supplies, wireless communications, infrared input, microphone input, or other devices. If desired, and if these ports 224 and/or 226 would be covered when the interface device 205 is attached to the electronic device 203, the interface device 205 may be equipped with similar external ports to ports 224 and/or 226, and internal circuitry may be provided in the interface device 205 to enable the user to plug the same additional devices into the interface device 205 as they might plug into the digital music player 203 and still take advantage of the same functions (e.g., to thereby allow the necessary data, signals, power, and/or information to pass through the interface device 205 to the user, to another output, and/or to the digital music player 203).

It should be appreciated that, while some specific embodiments of the invention described above relate to a digital music player 203, alternate examples of the invention may be implemented using any portable electronic device. For example, with some implementations of the invention, the athletic parameter measurement device 207 may be used in conjunction with a mobile telephone, a watch, a personal digital assistant, another type of music player (such as a compact disc or satellite radio music player), a portable computer, or any other desired electronic device. Still further, some implementations of the invention may alternately or additionally omit the use of the interface device 205. For example, the athletic parameter measurement device 207 may be configured to communicate using the Bluetooth wireless communication protocol, so that it can be employed with Bluetooth-capable mobile telephones, personal digital assistants, watches or personal computers. Of course, still other wireless or wired communication techniques could be employed while omitting the interface device 205.

It also should be appreciated that, while a specific example of an athletic parameter measurement device 207 has been described above for ease of understanding, any type of desired athletic parameter measurement device 207 can be employed with various embodiments of the invention. For example, with some implementations of the invention, the athletic parameter measurement device 207 may be a heart rate monitor, a blood oxygen monitor, a satellite positioning device (e.g., a Global Positioning Satellite (GPS) navigation device), a device for measuring the electrical activity of the user (e.g., an EKG monitor), or any other device that measures one or more physical parameters of the user. Still further, the athletic parameter measurement device 207 may measure one or more operational parameters of some device being manipulated by the user, such as the speed and/or distance moved on a bicycle; the speed and/or work performed using a treadmill, rowing machine, elliptical machine, stationary bicycle, or the like; and the speed and/or distance traveled using skis (water or snow), skates (roller or ice), or snowshoes or the like worn by the user; etc.

Also, while the athletic parameter measurement device 207 has been described as being separate from the digital music player 203 or other portable electronic device that receives the signals from the athletic parameter measurement device 207, with some implementations of the invention the athletic parameter measurement device 207 may be incorporated into the digital music player 203 or other portable electronic device. For example, some implementations of the invention may employ a music player, mobile telephone, watch or personal digital assistant that incorporates accelerometers, a satellite positioning device, or any other desired device for measuring athletic activity. Still further, it should be appreciated that various implementations of the invention may employ a plurality of athletic parameter measurement devices 207, incorporated into the digital music player 203 or other portable electronic device, separate from the digital music player 203 or other portable electronic device, or some combination thereof.

Data Collection And Display Tools

Figure 5:
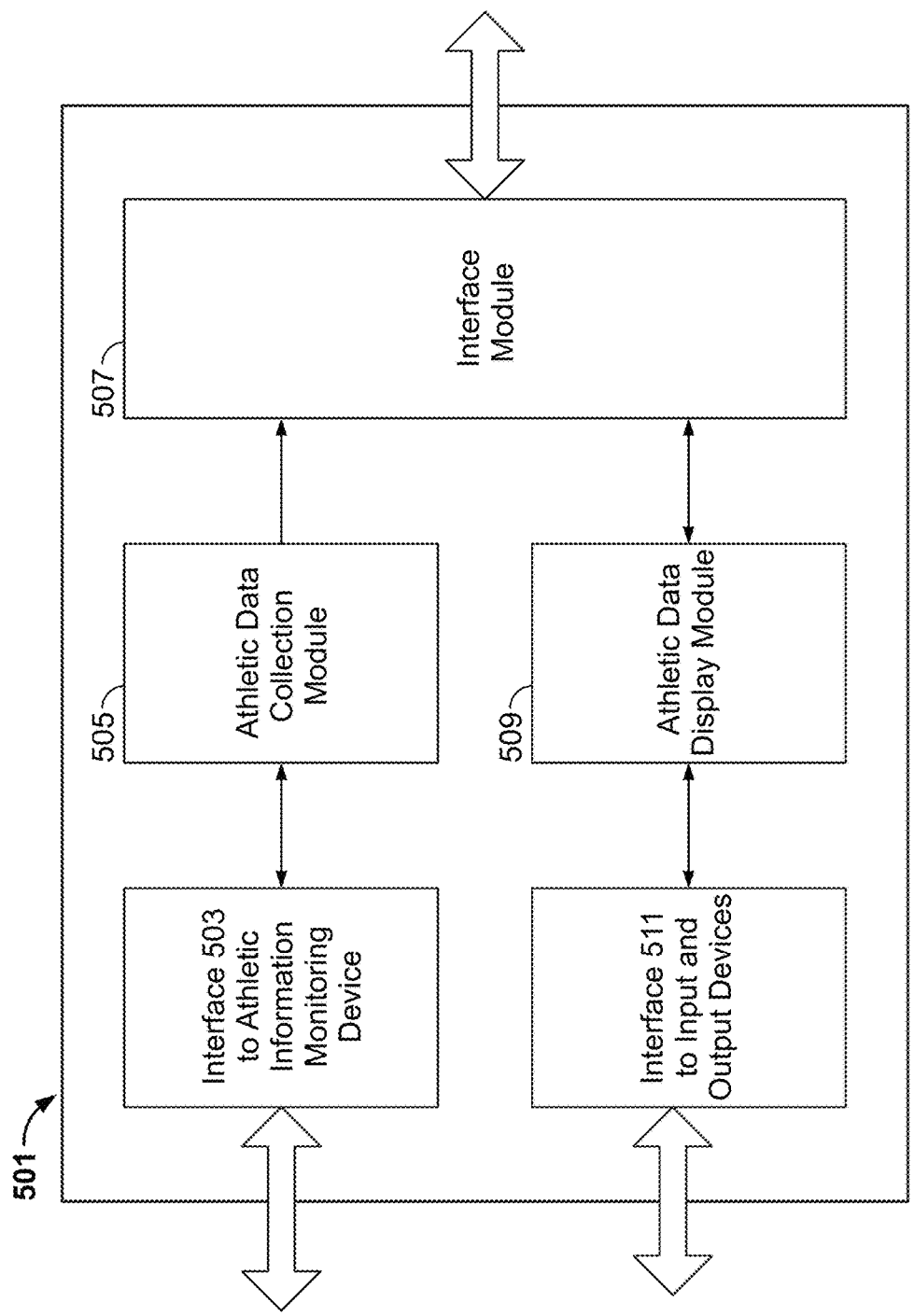
FIG. 5 illustrates an example of an athletic information collection and display device that may be employed to collect and/or display athletic data according to various implementations of the invention.

FIG. 5 illustrates an example of an athletic information collection and display device 501 that may be employed to collect and/or display athletic data according to various implementations of the invention. As will be discussed in more detail below, the athletic information collection and display device 501 may both collect and display athletic data. The athletic information collection and display device 501 may be implemented using any suitable variation of the computing device 101 previously described. In some situations, however, the information collection and display device 501 may be commercially implemented using a desktop or laptop personal computer using, e.g., a version of the Microsoft Windows operating system available from Microsoft Corporation of Redmond, Wash., a version of the Apple Macintosh operating system available for Apple Corporation of Cupertino, Calif., or a version of the Unix or Linux operating systems available from a plurality of vendors.

As shown FIG. 5, the athletic information collection and display device 501 includes an interface 503 for receiving data from the athletic information monitoring device 201. The interface 503 may be implemented using, e.g., electrical components, software components (such as application program interfaces (APIs)), or some combination thereof. The athletic information collection and display device 501 also has an athletic data collection module 505. With various examples of the invention, the athletic data collection module 505 may detect when the digital music player 203 or other portable electronic device storing one or more athletic data sets is connected to the athletic information collection and display device 501 through the interface 503 and establish a communication session with the digital music player 203 or other portable electronic device to retrieve the athletic data set or sets. In some implementations of the invention, the athletic data collection module 505 may delete athletic data sets from the digital music player 203 or other portable electronic device after the athletic data sets have been retrieved and stored at device 501.

With some examples of the invention, the athletic data collection module 505 may perform some further operations on the athletic data sets retrieved from the digital music player 203 or other portable electronic device. For example, if the athletic information monitoring device 201 can be employed to collect athletic information from different users, then the athletic data collection module 505 may additionally prompt the user to identify himself or herself (if this information was not previously obtained by the athletic information collection and display device 501). This identification information may then be included with the retrieved athletic data sets.

As previously noted, the athletic information collection and display device 501 typically will generate sets of athletic data from information measured by one or more athletic parameter measurement devices 207. With some embodiments of the invention, however, the athletic information collection and display device 501 may instead store the raw information provided by the athletic parameter measurement devices 207. With these embodiments, the athletic data collection module 505 may retrieve the raw information from the digital music player 203 or other portable electronic device, and then generate athletic data sets from the raw information itself. Of course, still other examples of the invention may divide functions relating to the generation of athletic data from the raw information measured by athletic parameter measurement devices 207 between the athletic data collection module 505 and the digital music player 203 or other portable electronic device as desired.

The athletic data collection module 505 may be implemented by, for example, software instructions executed by a computing unit 103 of a computing device 101. With some examples of the invention the athletic data collection module 505 may be implemented by a conventional software tool, such as a browser. Alternately, athletic data collection module 505 may be implemented by a purpose-specific software tool or by a conventional software tool enhanced to perform athletic data collection functions. For example, the athletic data collection module 505 may be implemented by a software tool that incorporates a conventional browser to perform a variety of functions. These functions may include, e.g., selecting, purchasing, and downloading music and video content in addition to collecting athletic data from a digital music player 203 or other portable electronic device.

Once the athletic data collection module 505 has collected the processed signals provided by the athletic information monitoring device 201, the athletic data collection module 505 transmits the athletic data set to an athletic data display configuration device 601 through an interface module 507. The athletic information collection and display device 501 may communicate with the athletic data display configuration device 601 through a conventional network, such as the Internet. With these configurations, the interface module 507 may be implemented using any conventional type of network interface, such as a network interface card. Of course, any type of desired hardware or software combination alternately may be used to allow the athletic data collection module 505 to send the collected athletic data to the athletic data display configuration device 601. With some implementations of the invention, the athletic data collection module 505 may automatically forward collected athletic data to the athletic data display configuration device 601. For example, the athletic data collection module 505 may attempt to forward collected athletic data to the athletic data display configuration device 601 immediately after collection, at a prescheduled interval, upon the detection of a network connection to the athletic data display configuration device 601, or some combination thereof. Alternately or additionally, the athletic data collection module 505 may prompt a user to specify when collected athletic data should be sent to the athletic data display configuration device 601.

Figure 6:
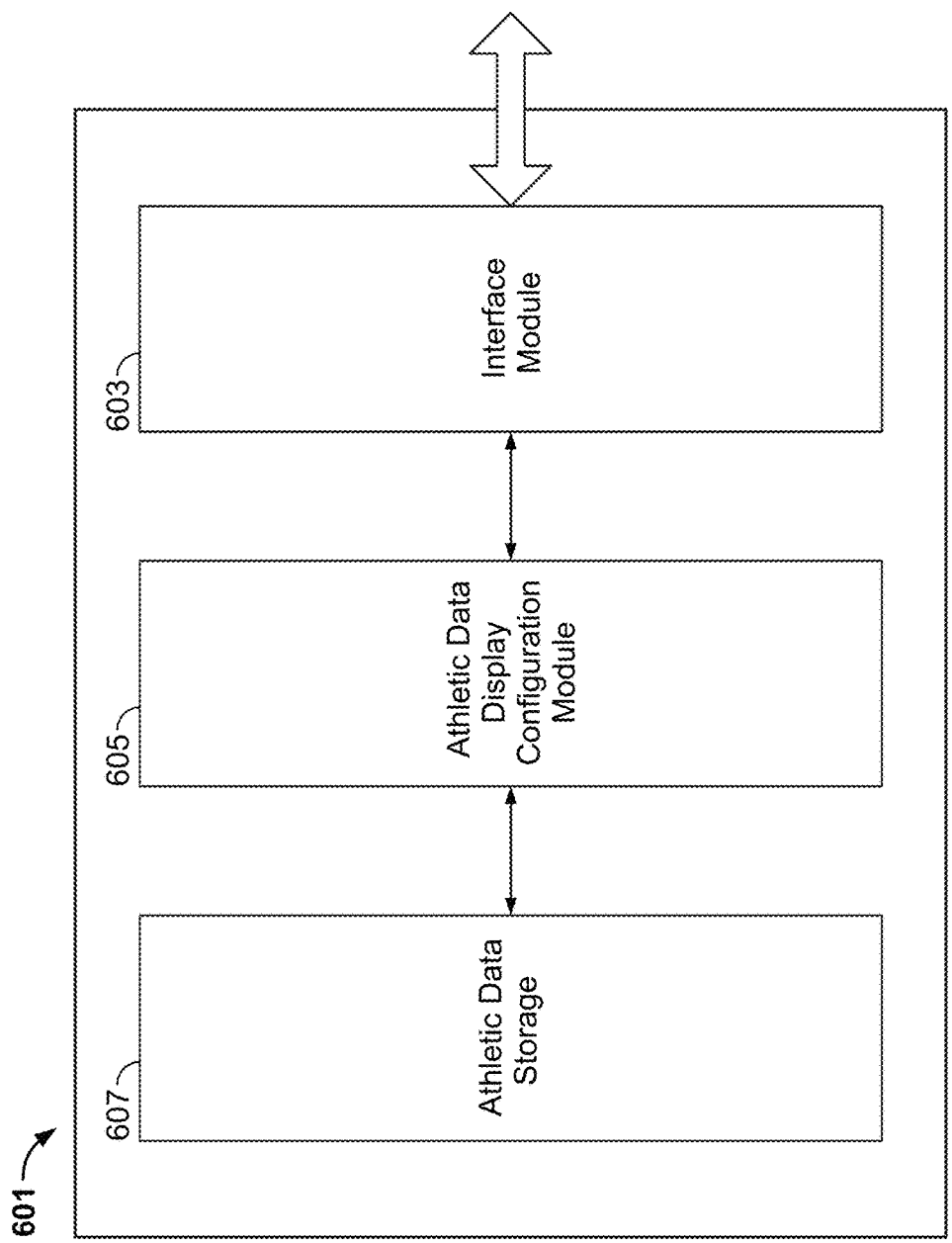
FIG. 6 illustrates an example of an athletic data display configuration device that may be employed according to various examples of the invention.

FIG. 6 illustrates an example of an athletic data display configuration device 601 that may be employed according to various examples of the invention. As seen in this figure, the athletic data display configuration device 601 includes an interface module 603 for communicating with the athletic information collection and display device 501. As previously noted, the athletic information collection and display device 501 may communicate with the athletic data display configuration device 601 through a conventional network, such as the Internet. With these configurations, the interface module 603 may be implemented using any conventional type of network interface, such as a network interface card. Of course, any type of desired hardware or software combination alternately may be used to allow the athletic data display configuration device 601 to communicate with the athletic information collection and display device 501.

The athletic data display configuration device 601 also includes an athletic data display configuration module 605, and an athletic data storage 607. When the interface 603 of the athletic data display configuration device 601 receives athletic data from the athletic information collection and display device 501, it provides the received athletic data to the athletic data display configuration module 605. The athletic data display configuration module 605 may then store the athletic data in the athletic data storage 607 for future use. As will be discussed in more detail below, the athletic data display configuration module 605 also will retrieve athletic data from the athletic data storage 607, and configure the retrieved athletic data for display through one or more user interfaces in a manner that is meaningful to a user.

Returning now to FIG. 5, when a user wishes to view information relating to his or her athletic activities (or the athletic activities of another, as will be discussed in more detail below), the user submits this request to the athletic information collection and display device 501. More particularly, the user can employ conventional input and output devices, such as a keyboard, mouse, display and the like. The display request is then provided to an athletic data display module 509 through a conventional interface input/output interface 511. As well known in the art, the interface input/output interface 511 may be implemented using any desired combination of hardware and software components, such as conventional application programming interfaces (APIs) used to detect and process input from input devices and to send data to and otherwise control output devices.

With some examples of the invention, the athletic data display module 509 may be implemented using any conventional tool for receiving input to request and control the display of data, and then subsequently displaying the data in the manner requested. For example, the athletic data display module 509 may be implemented using a conventional browser program, such as Microsoft Internet Explorer, Mozilla Firefox, or Opera executing on a computing unit 103. With still other embodiments of the invention, the athletic data display module 509 may be implemented using a conventional browser program that has been enhanced by one or more display tools, such as an ActiveX plug-in, a Java script or a version of the Macromedia Flash Player or Adobe Flash Player, available from Adobe Systems Incorporated of San Jose, Calif. In still other embodiments of the invention, the athletic data display module 509 may be implemented, for example, by a purpose-specific software tool for displaying athletic data.

As will be discussed in more detail below, when a user activates the athletic data display module 509, he or she is provided with a user interface prompting the user to select what collected athletic data he or she wishes to view, the format in which the user wishes to view the collected athletic data, etc. This user interface may be generated by the athletic data display module 509, the athletic data display configuration module 605, or some combination thereof. When a user employs the provided user interface to submit a request to view athletic data, the athletic data display module 509 relays the request to the athletic data display configuration module 605. In response, the athletic data display configuration module 605 configures the requested athletic data for display by the athletic data display module 509. For example, as will be discussed in more detail below, a user may request to view the total distance run by a user for each day in a one week period. In response, the athletic data display configuration module 605 will retrieve the relevant distance data from the athletic data storage 607. It will then configure the retrieved distance data to be displayed through a desired image (e.g., a bar graph) and provide the configured athletic data to the athletic data display module 509 for display to the user.

It should be noted that, with some embodiments of the invention, the data display configuration functions may be divided between the athletic data display module 509 and the athletic data display configuration module 605. For example, if the athletic data display module 509 is implemented by a simple browser, then the athletic data display module 509 may serve as a "thin client" for the athletic data display configuration module 605. That is, all of the data display configuration functions may be performed by the athletic data display configuration module 605. The athletic data display module 509 will then only display the information provided to it. Alternatively, if the athletic data display module 509 is implemented by a purpose-specific software tool, then most or all of the data display configuration functions may be performed by the athletic data display module 509. With these examples, the athletic data display configuration module 605 may be used only to store and retrieve athletic data from the athletic data storage 607.

User Activity Monitoring Device

Figure 7A:
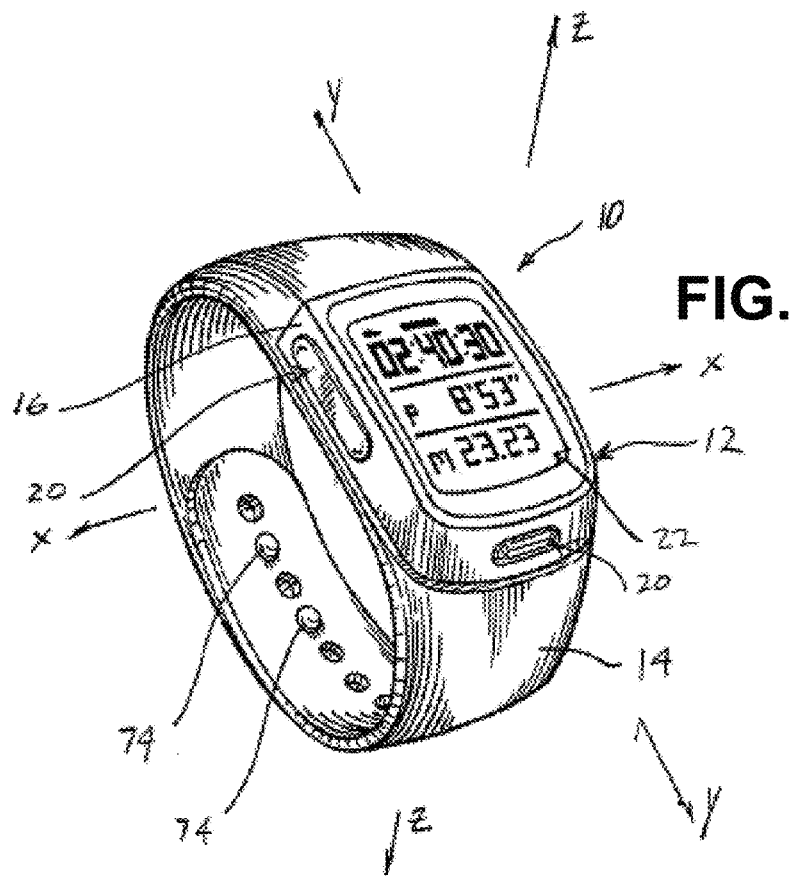
FIGS. 7A and 7B illustrate an example of an athletic activity monitoring device according to one or more aspects described herein.
Figure 7B:
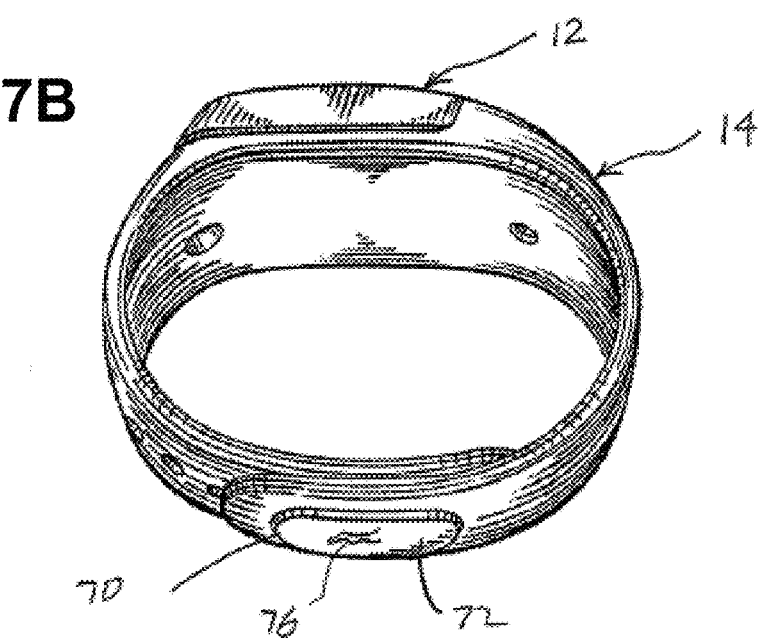

FIGS. 7A and 7B generally show an athletic activity monitoring device or watch that may be used to track a user's athletic activity or non-athletic activity and/or activity point accumulation. The device is generally designated with the reference numeral 10. While the watch 10 has traditional uses such as incorporating a chronograph for general timekeeping, as explained in greater detail below, the watch 10 has unique functionality for athletic and fitness use such as monitoring athletic performance of the user. The watch 10 generally includes a portable electronic module 12 removably connected to a carrier 14 or strap member in the form of a wristband 14 in an exemplary embodiment.

The structure of the watch 10 will first be described followed by a description of the operation of the watch 10. However, as explained in greater detail below, it is noted that the watch 10 is capable of wirelessly communicating with various sensors worn by a user to record and monitor athletic performance of a user. The sensor(s) can take various forms. For example, the sensor may be mounted on the shoe of a user and include an accelerometer. The sensor may have various electronic components including a power supply, magnetic sensor element, microprocessor, memory, transmission system and other suitable electronic devices. The sensor may be used in conjunction with other components of the system to record speed and distance among other parameters of athletic performance. In exemplary embodiments, the sensor can be a sensor as disclosed in U.S. Publications No. 2007/0006489; 2007/0011919 and 2007/0021269, which are incorporated by reference herein and made a part hereof. Additionally, the sensor may be a component of a heart-rate monitor worn by a user (e.g., a heart-rate strap worn around the user's chest). Thus, in various arrangements, the watch 10 may communicate with shoe sensors and heart rate sensors among other types of sensors. The watch 10 may further communicate with only one of the shoe sensor and heart rate sensor depending on a user's preference. The watch 10 may also include component(s) such as a three-axis accelerometer to monitor speed and distance of a user/runner without the need for the shoe sensor. The watch 10 has communication capabilities with remote locations for receiving and transferring data relating to athletic performance monitoring. Alternatively or additionally, activity sensors such as accelerometers, pedometers, heart-rate sensors and the like may be included within watch 10. Accordingly, a sensor separate from watch 10 might not be needed. Sensors might also be included within other devices such as device 201 of FIG. 2 to reduce or eliminate the need for external sensors, although such sensors might still be operable with the monitoring devices.

As further illustrated in FIGS. 7A and 7B, the portable electronic module 12 includes various components supported by a housing 16, the components include a controller 18 having a suitable processor and other known components, an input device assembly 20, an output device assembly 22, and a communication connector 24, which may be considered a part of the input device assembly 20 and/or the output device assembly 22 in various embodiments. The communication connector 24 may be, for instance, a USB connector 24. The controller 18 is operably connected to the input device assembly 20, the output device assembly 22 and the communication connector 24. As explained in greater detail below, the electronic module 12 may also include a GPS ("Global Positioning System") receiver and associated antenna operably connected to the controller 18 for incorporating various GPS features.

The carrier 14 is generally in the form of a wristband 14 having a central portion between a first end portion and a second end portion. The wristband 14 may include a first member and second member generally molded or connected together. The wristband 14 is flexible to fit around a user's wrist. In one exemplary embodiment, the wristband 14 may be injected molded of a flexible polymeric material. The wristband 14 has receiving structures for connection to the portable electronic module 12.

According to one or more aspects, the first end portion has a pair of holes to accommodate a removable closure 70 used to fasten the wristband 14 to a wrist of a user. To this end, the removable closure 70 cooperates with the plurality of holes in the wristband 14. The removable closure 70 has a plate member 72 and a plurality of posts 74 extending generally in a perpendicular direction from the plate member 72. In the exemplary embodiment, the plate member 72 has two posts 74. To wear the wristband, first the removable closure 70 is connected to the first end portion of the wristband strap wherein the pair of holes is provided to receive the posts 74. The wristband 14 is positioned around the user's wrist and the posts 74 are inserted into holes provided on the second end portion of the wristband 14 as can be appreciated from FIG. 7A. After the posts 74 are inserted into the pair of holes of the first end portion of the wristband 14 and the plurality of holes of the second end portion of the wristband 14, the first end portion and second end portion of the wristband 14 overlap one another. With the use of a pair of posts 74, the removable closure 70 allows for a secure connection and greater flexibility in connection providing for a greater adjustment to accommodate for a range of wrist sizes.

Additionally, the plate member 72 can have indicia 76 thereon. The plate member 72, when attached to the wristband 14 faces away from the wristband 14 wherein the indicia 76 can be viewed by others. Because the removable closure 70 is easily removable, the closure 70 can be used as a memento, different closures can be provided and used with the wristband 18. Thus, removable closures 70 having different indicia can be provided and used as a keepsake, memento, or a reward for accomplishing a goal, participating in a race, or otherwise achieving a certain level of fitness. Indicia can take various forms including wording, graphics, color schemes, textures, or other designs etc. Additional details relating to such wearable user activity monitoring devices may be found in U.S. application Ser. No. 12/767,288, entitled "Athletic Watch" and filed Apr. 26, 2010.

According to one arrangement, the watch 10 may be a championship device configured to receive data from one or more event monitoring devices. For example, watch 10 may include an RFID tag or RFID sensor that is configured to interact with a corresponding RFID tag or sensor in one or more event devices. In running competitions, for instance, a track may include a mat that is configured to generate an electromagnetic field for triggering a user's device (e.g., watch 10) to begin recording time. In another example, one or more event monitoring devices may track the user's RFID tag as the user progresses along the race course. At the end of the race, the user's race statistics may be transmitted to his or her device. The user may then view the information through the device.

User Activity Environment

Figure 8A:
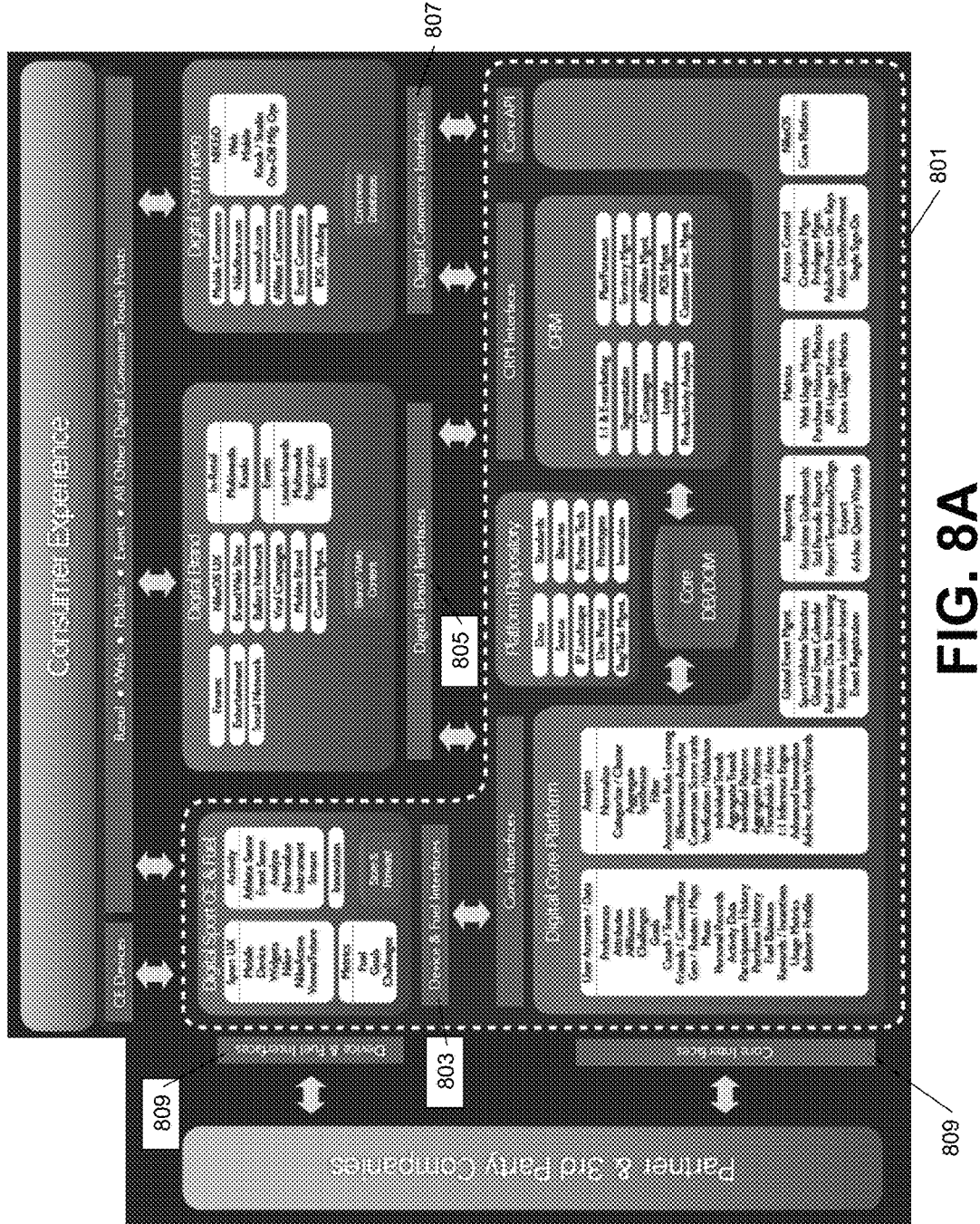
FIG. 8A-8D illustrate an athletic activity monitoring system and engines thereof that may be used in an athletic activity monitoring environment according to one or more aspects described herein.

In addition to the monitoring of athletic activities, a user's non-athletic activities may also be monitored and used to customize a user's experience with a service to improve their interest and motivation. Using such systems and methods, a user may be further motivated to engage in athletic activities by incorporating other facets of a user's life into a fitness-oriented environment. FIGS. 8A-8D illustrate computing environments through which both athletic and non-athletic activities may be monitored, collected, stored, analyzed and rewarded according to various aspects of the present disclosure. For example, FIG. 8A illustrates that athletic performance monitoring system 801 may provide a variety of services and features including a platform that maintains user account information; analyzes user behavior and performance; manages events in which users may participate; reports information to other systems, applications and devices; measures user activity; and controls access to stored information. For example, system 801 may allow users to register with system 801 to track and monitor their athletic performance and other types of activity. Accordingly, users may allow system 801 to collect user information and activity information such as workout data, on-line browsing statistics, shopping preferences and the like to formulate a digital portrait of the user. This information may further be analyzed to identify interests, trends and behavior to better customize the user's experience with system 801 and/or the services provided thereby.

According to one or more aspects, system 801 may further include interfaces 803 that allow remote devices (e.g., watch 10 of FIGS. 7A and 7B) to submit and receive information. For example, a user's wristband may be equipped with athletic activity monitoring sensors and a display. Accordingly, a user's athletic activity may be determined by the athletic activity monitoring sensors and displayed on the display to allow a user to track his or her progress. The detected athletic activity may then be transmitted to system 801 for analysis and storage. System 801 may further interface with various sources of information in order to increase awareness of the services provided by system 801 and to reach a wider audience. For example, system 801 may submit content such as articles, posts in forums, entertainment content and/or social network content that may be branded with the various services provided by system 801 to other sites or systems through interfaces 805. Furthermore, system 801 may include digital commerce interfaces 807 that provide an outlet for consumers to purchase products and services. These products and services may be produced by, offered by or otherwise associated with a company or organization sponsoring the services provided through system 801. Additionally or alternatively, the products or services sold through such digital commerce outlets may be tied or provide access to the services of system 801. For example, shoes may be sold with transmission devices that are configured with protocols to communicate with system 801.

System 801 may further allow partner and third party entities to interface with system 801 to provide additional products or services that leverage and/or interoperate with the features offered by system 801 through interfaces 809. For example, a partner or third party entity may produce sensors or wearable athletic performance monitoring devices that are compatible with the services offered by system 801. In particular, the wearable monitoring devices or sensors may integrate one or more features or services provided by system 801 such as viewing the user's workout information in conjunction with a competitor's workout information (e.g., competitor workout information may be retrieved remotely from system 801 through the wearable device or sensor). Compatibility may include operation under secure protocols understood and/or required by system 801. In another example, athletic activity equipment such as tennis balls, basketballs, tennis rackets, lacrosse sticks, gold clubs, golf balls, soccer balls, baseballs, football pads and the like may be produced by third party or partner entities with technology that allows interfacing with system 801. For example, tennis balls may include sensors to detect a force of a user's stroke. Such information may be transmitted from the tennis ball to another device or to system 801 for analysis, storage and/or monitoring. In another example, football pads may include pressure sensors to indicate an amount of force with which football players are being hit or that the players are exerting.

System 801 may, in one or more arrangements, include a marketing engine that leverages activity information collected from users to identify consumer interests, activity patterns and trends. This information may be used to determine what information to display to users and what products or services to advertise. For example, if a user frequently plays basketball and purchases basketball related equipment, a service may be able to better target the user with advertisements that relate to basketball events, sales and products. In another example, if a user frequently tracks calories (e.g., as opposed to miles or pace), a service may target the user with weight loss services and/or products. Activity analysis and marketing customization is further described in co-pending U.S. application Ser. No. 12/854,283, entitled "Intelligent Display of Information in a User Interface," filed on Aug. 11, 2012.

Figure 8B:
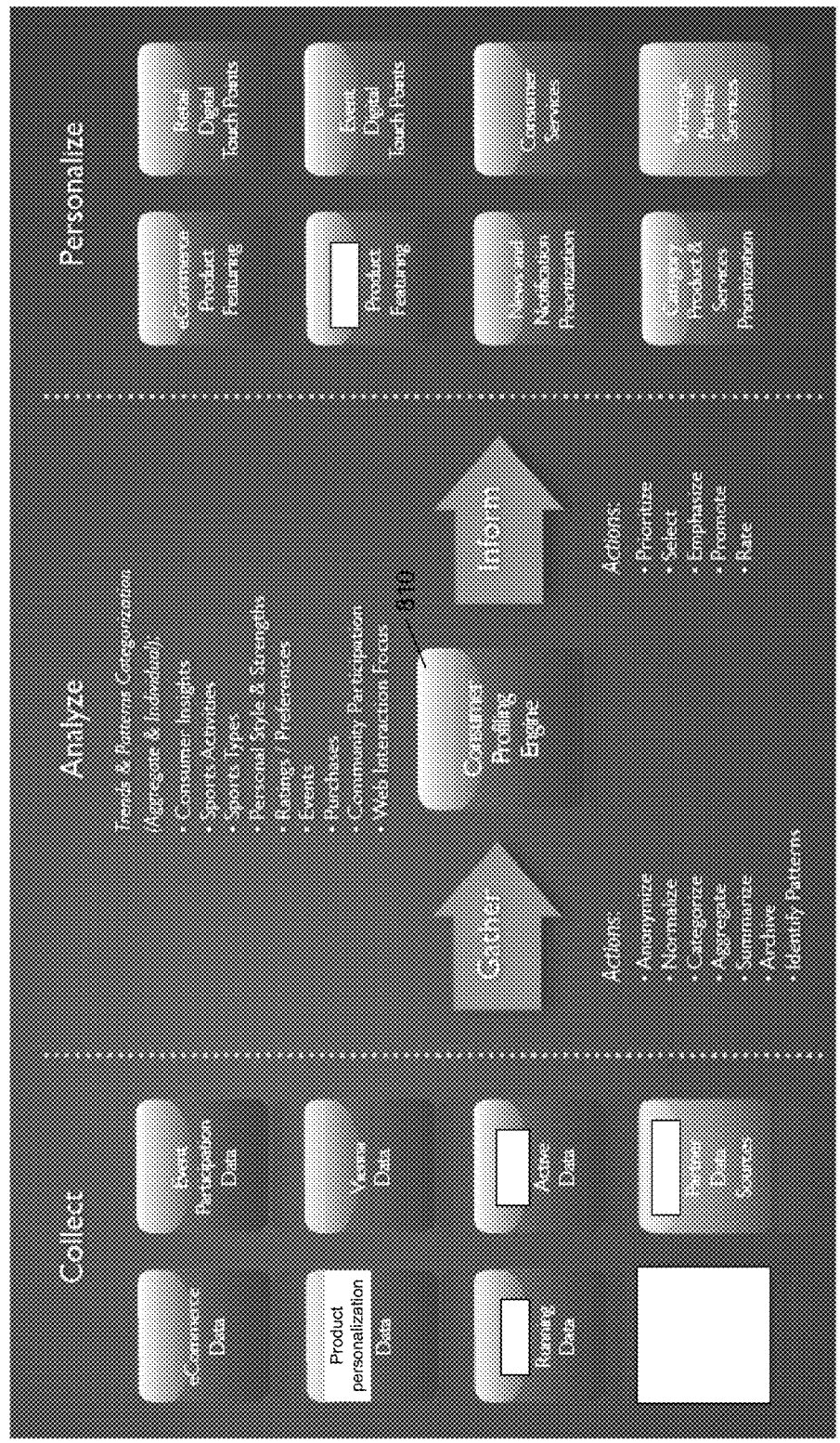

System 801 may use various analytical engines that are configured to process the submitted athletic activity information (or other types of information such as shopping behavior and browsing trends) to customize the user experience. In one example, a system may include a consumer profiling engine configured to customize content based on a user interests and other aspects of a user's profile. FIG. 8B illustrates an example environment in which consumer profiling engine 810 may collect user information and use that information to personalize the user's experience. For example, consumer profiling engine 810 may collect eCommerce data, event participation data, workout information, music selection information and the like to produce insights into various aspects of the user. Such insights may include user interests in sports, personal styles and strengths, user preferences for events or event locations, shopping and/or browsing interests, community participation (e.g., social networking membership) and the like. Based on these determined insights, a system such as system 801 (FIG. 8A) may customize various aspects of a user's experience using system 801 including suggesting various products (or a color scheme thereof), services, events and the like for the user. For example, a user's homepage on an athletic performance monitoring site may be customized with information including articles, advertisements, messages and the like that is determined to be of particular interest to the user. In another example, information may be prioritized for display to the user based on the user profile. According to one arrangement, metadata may be stored in association with products and used to compare and match against keywords corresponding to interests, insights or preferences determined from and associated with a user. Such matching and customization may also be performed on a group level, for example, based on demographics, location, preferred sport, and the like. Accordingly, products, events and services may be identified for a particular category or group of people based on shared interests or characteristics by matching those interests or characteristics to the determined insights.

Figure 8C:
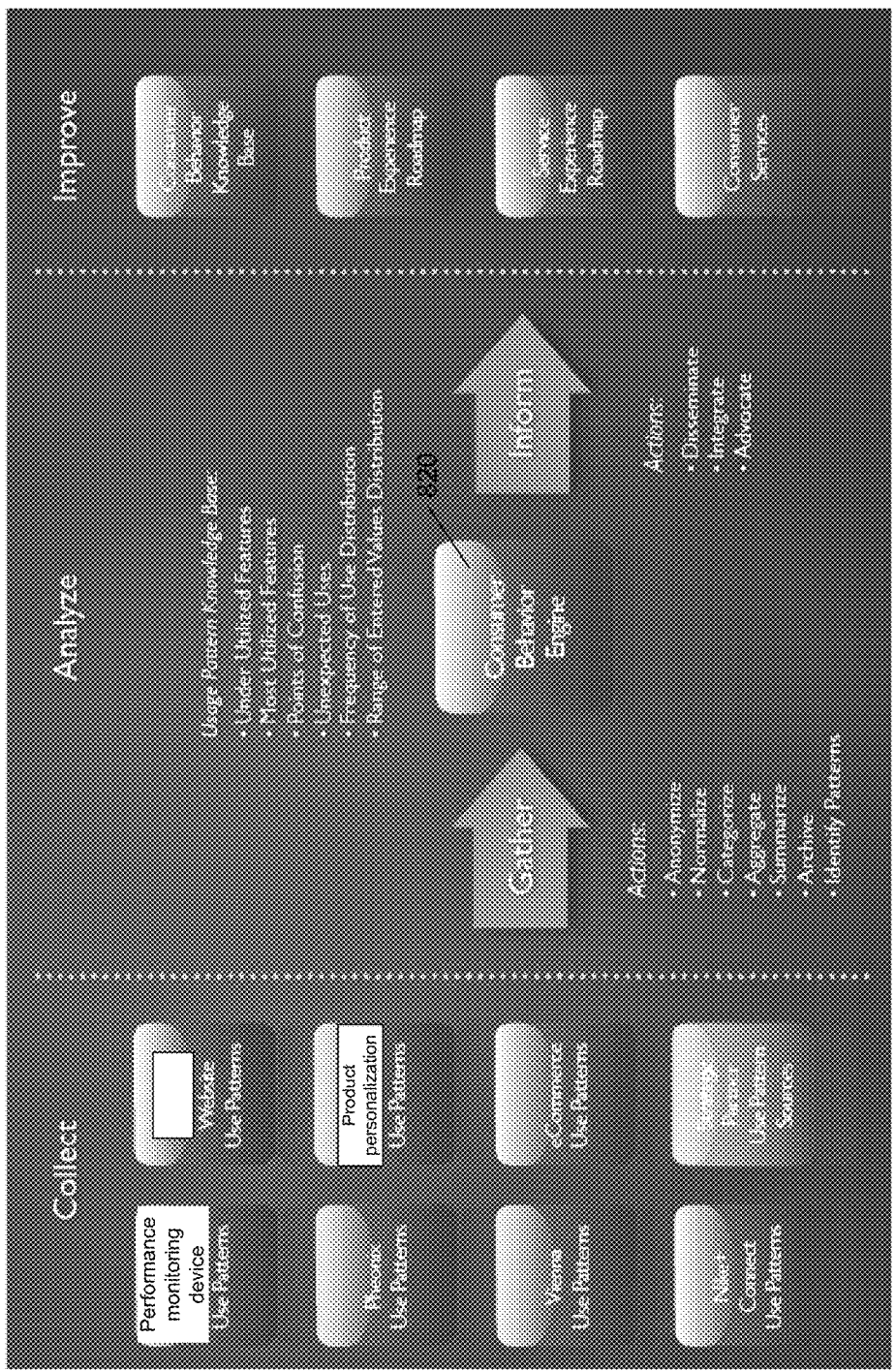

System 801 may further include a consumer behavior engine. FIG. 8C illustrates an example consumer behavior engine 820 that may be used to collect information about user behavior and to use such behavior to optimize consumer services offered to the user, customize a navigation flow of various interactive sites and services and to increase a customer behavior knowledge database. In one example, system 801 may modify a site content or navigation flows if consumer behavior engine 820 identifies that a user frequently uses a particular functionality that is not displayed on a main page. That is, system 801 may customize the user's main page by adding the frequently and/or recently used functionality. Additionally or alternatively, a produce or service provider may customize their product line or manufacturing capabilities based on the results of the consumer behavior engine 820. This may help a service or product provider meet demands and maximize profits. Further, in some arrangements, products, services or events may be showcased at various venues such as retail stores based on the consumer behavior analysis. In one example, an electronic bulletin board of a retail store may display advertisements based on what has been determined to be popular based on the collected user behavior information. In other arrangements, the electronic bulletin board may update its display on an individual basis. The individual may wear or carry some electronic identifier that may be detected by the bulletin board. Upon detecting the individual, the bulletin board may retrieve preference or characteristic information for the user to identify products, services and/or events to advertise on the board.

Figure 8D:
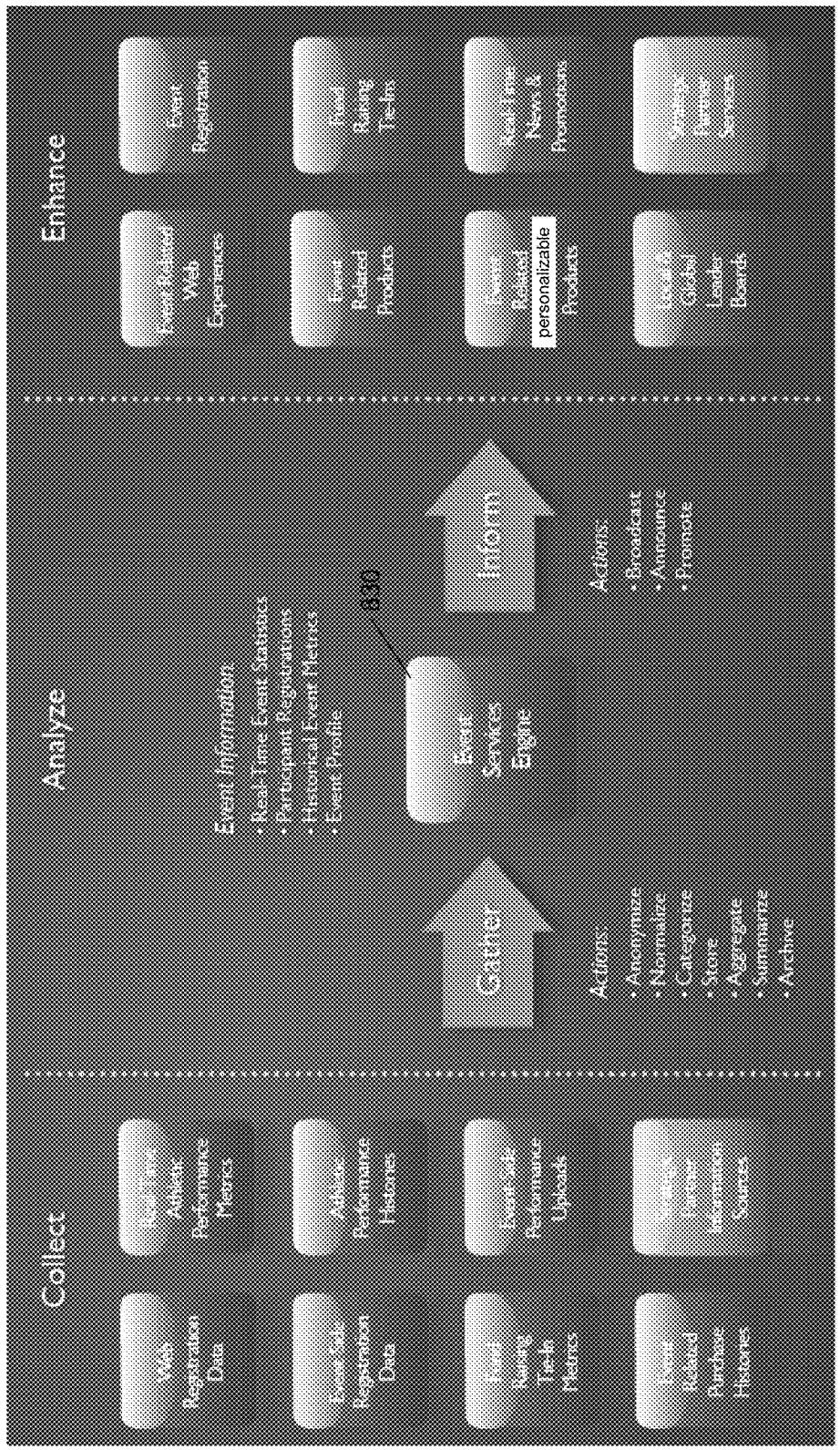

In one or more arrangements, system 801 may also include an event services engine that is configured to create events based on information collected from users, their behavior and experiences. FIG. 8D illustrates an example event services engine 830 that collects various types of information including event registration information, athletic performance metrics, athletic performance histories, fundraising information, event related purchase histories and the like to evaluate the effectiveness and draw of past events. Based on the successes and failures thereof (identified through the analysis of the collected information), event services engine 830 may create events that specifically target various types of audiences and participants or to achieve a specified objective. In one example, event services engine 830 may create events that are designed to maximize fundraising. In yet another example, event services engine 830 may create events that seek to maximize attendance.

Using the above analytical engines, a user's experience with a fitness-oriented service or system (e.g., system 801 of FIG. 8A) may be improved. In particular, users that are not inclined to exercise may be more willing or motivated to access the fitness-oriented service or system since the service pages or interfaces may be customized to the user's particular interests. In some examples, the customization of a user's experience may include identifying content that is related to a non-athletic activity interest of the user (e.g., entertainment news, music, movies, etc.).

Activity Points

As noted above, the information collected using a system such as system 801 of FIG. 8A may be used to provide various ways to motivate and encourage athletic activity among users. According to one or more aspects, measures of athletic activity may be converted into a form of currency that may be used to purchase products, measure an overall athletic activity level, receive rewards, achieve goals, obtain discounts, use in video games or other applications and the like. For example, 400 calories burned during a running workout may be converted into 50 activity points based on an 8-1 calorie-to-activity point conversion rate. In another example, activity points may be rewarded for running activities based on a distance run rather than or in addition to the number of calories burned. In another example, a number of steps taken during a walking workout may be converted into athletic activity points based on a 200 step to 1 activity point conversion rate. In yet another example, activity points may be calculated for a weightlifting exercise based on the amount of weight lifted and a number of repetitions performed using that weight. As other examples, time involved at a predetermined exertion level and/or improving on a personal best may result in activity point awards.

Different conversion factors, rates and algorithms may be applied to different types of athletic activity. In one or more arrangements, a conversion rate or algorithm may be selected based on user characteristics such as weight, gender, height, age, resting heart rate, an activity level and/or combinations thereof. Conversion rates may also be stored and implemented within various types of gym equipment. Accordingly, a gym device may calculate a number of activity points earned and transmit that information to the user's monitoring device. Alternatively or additionally, the gym device may provide the conversion rate and the athletic measures to the monitoring device, thereby allowing the monitoring device to perform its own calculation/conversion. In some instances, if a user fails to achieve a goal or reach an objective, points may be deducted from the user.

According to one or more additional aspects, a conversion rate or algorithm may be determined based on a user's athleticism score such as a SPARQ rating. Alternatively or additionally, data used in deriving the SPARQ rating may be evaluated in determining a number of points to award or deduct from a user.

Athletic activity, as described herein, may be monitored and tracked using an athletic activity performance monitoring device such as performance monitoring device 201 of FIG. 2 or watch 10 of FIGS. 7A and 7B. Once athletic activity has been recorded by monitoring device 201, device 201 may convert the recorded athletic activity into activity points. For example, upon completion of the workout, a user may select an option to display the number of activity points earned through the workout. Alternatively or additionally, the athletic activity may be converted into activity points on-the-fly. For example, as mileage or steps are accumulated or as calories are burned during a workout, the athletic activity performance monitoring device 201 may determine an equivalent number of activity points. These activity points may be displayed on a display, e.g., of digital music player 203, so that a user may be provided with additional motivation to keep working out. That is, since athletic activity points may be used as a form of currency, a user may be more motivated to continue working out to be able to purchase a product or service that costs a certain number of activity points sooner.

In some arrangements, activity points may also be earned through activities other than athletic activities. For example, user purchases, visiting advertiser's websites, signing up for or participating in an event and the like may earn a user activity points. Points may also be deducted from a user for various activities. For example, the types of food a user eats may affect the user's point balance. Accordingly, in one particular example, if a user eats something considered unhealthy such as a donut, a certain number of activity points may be deducted form the user's account. The deduction may correspond, in one or more arrangements, to a number of calories associated with that food product. In contrast, if a user consumes food that is considered to be healthy and/or nutritious, the user may earn points based on that activity as well. Thus, in one specific example, a user may consume two servings of vegetables. Accordingly, the user may earn a certain number of points for consuming those two servings of vegetables. A formula may be used to convert the number of calories associated with the food product to a number of activity points earned or lost (e.g., 10 calories=1 activity point). Different conversion formulas may be used for unhealthy foods (or points to be deducted) versus healthy foods (or points to be earned). In one example, points may be lost at a faster rate (e.g., more points lost per calorie consumed) than points earned. In another example, points may be earned at a faster rate than points lost.

Display of Activity Points and Performance Information

Figure 9:
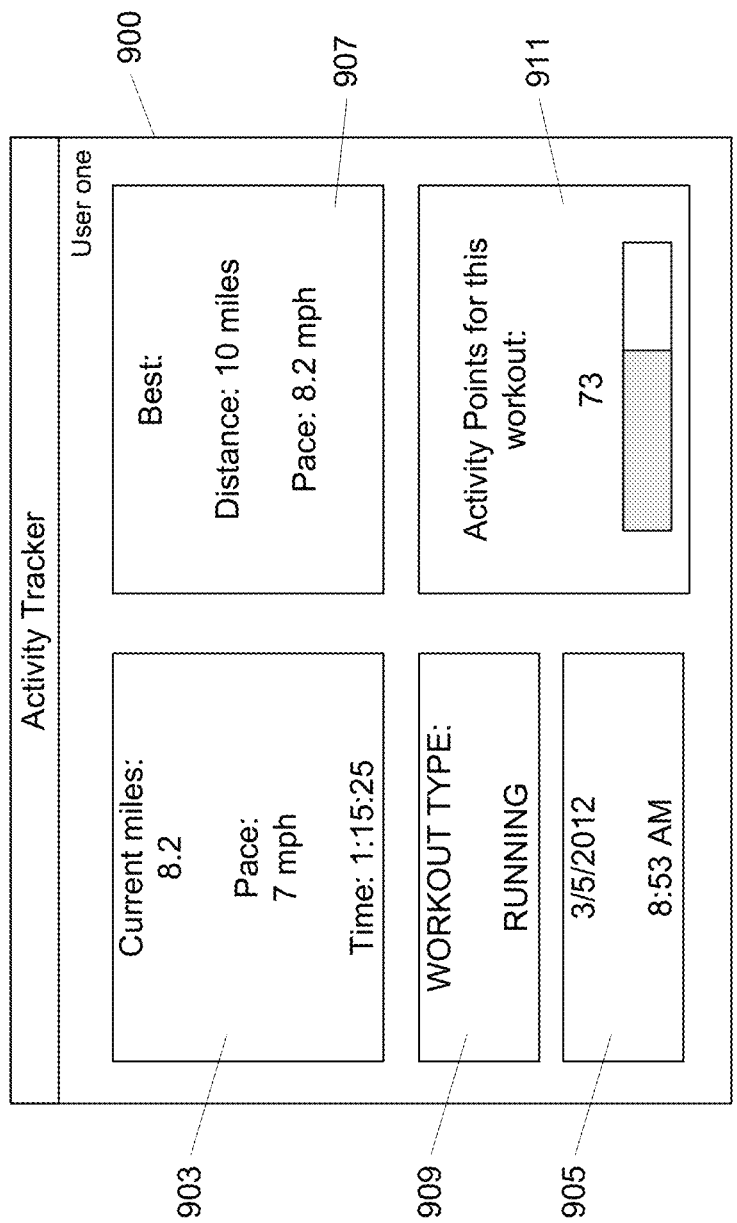
FIG. 9 illustrates an example user interface that may be displayed by an athletic performance monitoring device or system according to one or more aspects described herein.

Activity information including athletic and non-athletic activity measures and earned activity points may be displayed for user review and management in a variety of manners. FIG. 9 illustrates an interface 900 (e.g., of a display of athletic performance monitoring device 201 of FIG. 2 and/or watch 10 of FIGS. 7A and 7B) configured to convey athletic performance information before, during and/or after a workout. For example, in interface 900, athletic activity measures including, for example, a number of miles run, calories burned, heart rate, amount of time, amount of force used (e.g., in weightlifting or step exercises), steps taken and/or combinations thereof may be displayed in a first portion 903. Other information may be displayed simultaneously or sequentially with the athletic activity measure 903. For example, a current time and date may be displayed in a second portion 905 of interface 900. A third portion 907 of interface 900 may display information relating to a user's best workout and/or goal information. The information displayed in portion 907 may depend on the type of workout in which the user is currently engaged and/or the information that the user has selected for display as athletic activity measure 903. For example, if the user elects to display an amount of time run or exercised, portion 907 may display the greatest amount of time the user has ever exercised (or within a predefined amount of time such as the last month, among all recorded data, last year, last week, last 10 workouts, etc.) or a current goal that the user is attempting to accomplish or reach. The type of workout may also be identified in portion 909 of interface 900.

The user may configure interface 900 in a variety of ways including selecting the types of information displayed therein. In one example, the user may elect to display a corresponding or estimated number of activity points 911. Activity points 911 in interface 900 might only be an estimate since the number of activity points awarded by a sponsoring organization may require final verification and approval. For example, a sponsoring organization may perform a final determination of the number of points to be awarded upon reviewing a user's workout information. Activity points 911 may correspond to a total number of activity points of a particular type or grade, available to a user (e.g., unspent activity points accumulated from a current workout in addition to previous workouts), or accumulated during the current workout session. One or more aspects of interface 900 may be modified and configured according to user preferences. For example, a user may choose to turn off the activity point tracker 911. In another example, a user might not wish to display the current time and date 905. In other examples, a user may rearrange the placement, size and appearance of various information portions to suit the user's viewing preference.

The appearance of information displayed in a user interface such as interface 900 of FIG. 9 may change depending on one or more variables of a workout. For example, if a user enters a heart rate range that is at or above 90% of the user's resting heart rate, the displayed heart rate may change color, font, size and/or combinations thereof. In another example, a workout metric may change color upon reaching or approaching various targets (e.g., miles, calories, steps), exceeding a personal best, exceeding or falling below a target pace, etc. Other portions of an interface (e.g., beyond the workout metric) may also change in appearance. In one example, the entire interface may flash or rapidly alternate between two colors upon detecting a triggering event.

Figure 10A:
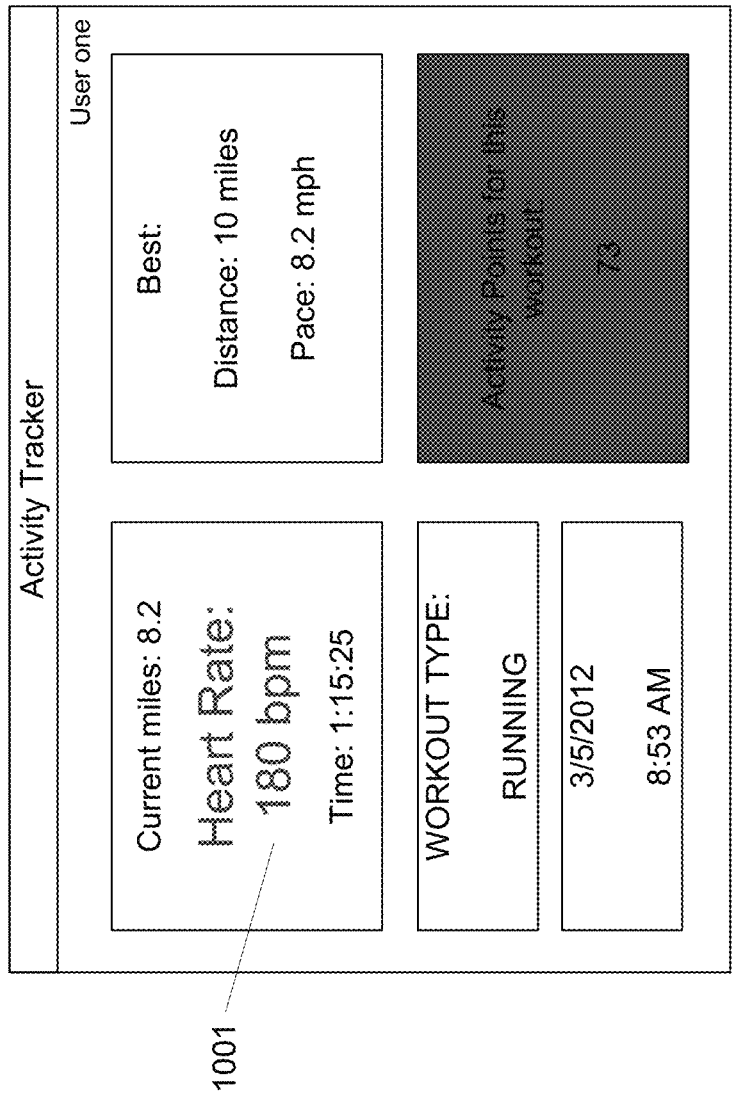
FIGS. 10A-10C illustrate changes to an user interface displaying athletic activity information upon detection of a triggering event according to one or more aspects described herein.
Figure 10B:
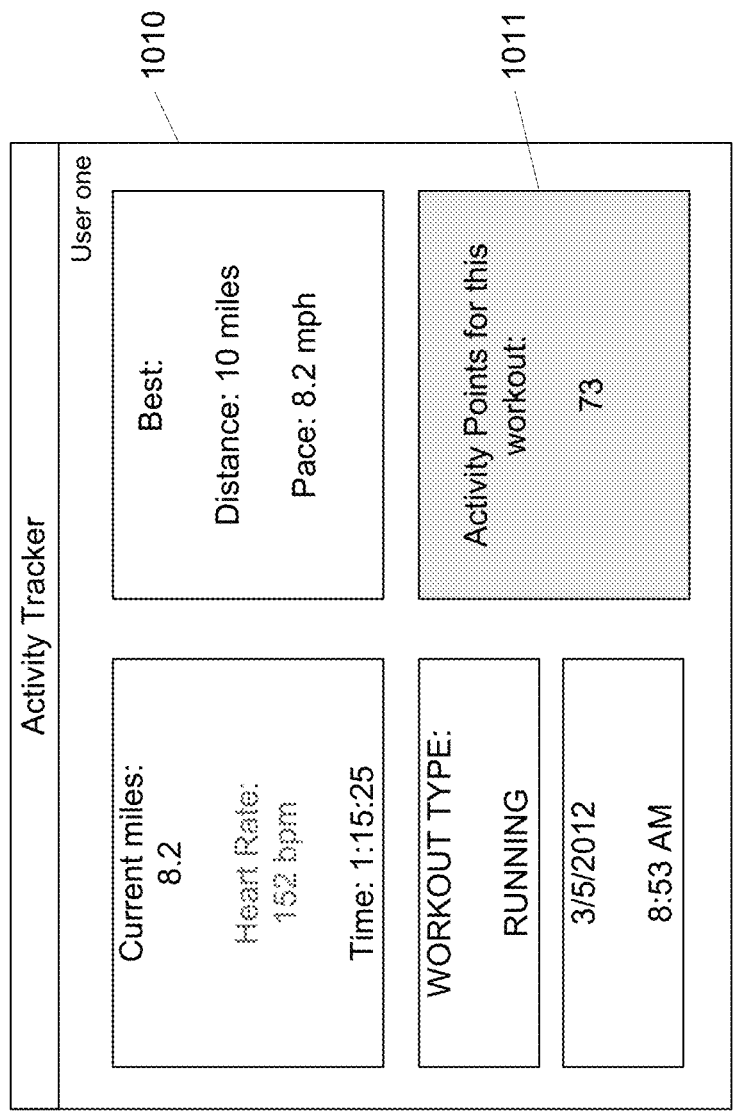
Figure 10C:
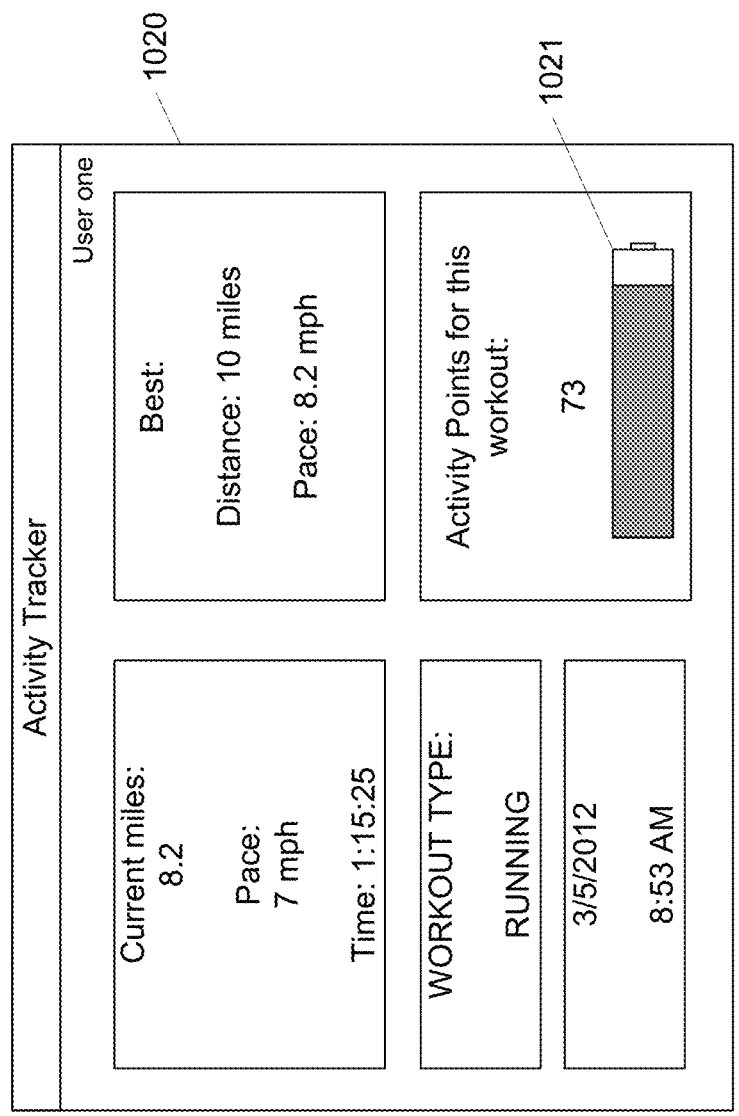

FIGS. 10A-10C illustrate various examples of how portions of an athletic activity performance monitoring interface may change upon detecting a triggering event. In FIG. 10A, for example, a user's heart rate 1001 is displayed in an alternate color and in an increased font size upon detecting the user's heart rate exceeding a predefined limit. In particular, the user's heart rate 1001 is displayed in red and in 12 point font. In contrast, when a user's heart rate 1001 is below the predefined limit, the user's heart rate may be displayed in green or black and in 9 point font. Alternatively or additionally, heart rate 1001 may blink or flash to further alert the user to the detected condition. If the user's heart rate 1001 drops below a second threshold, the user may be similarly alerted using a change in color, font size, font or the like. This may help alert the user to when he or she is outside of a preferred exercise heart rate range. Other appearance characteristics may also be modified including font style (e.g., bold, italic, underlined), capitalization (all caps, small caps), background color, text and/or graphic position and the like.

FIG. 10B illustrates another example in which an activity point portion 1011 of interface 1010 may change in appearance upon the occurrence of a triggering event. A user, for instance, may set a target activity point. This target activity point may correspond, in one or more examples, to a number of activity points required to obtain a particular reward or to achieve some other goal (e.g., in a video game). In one or more examples, the goal or reward (not shown) that the user is trying to achieve may be displayed or represented in interface 1010. Alternatively, the target activity point level may be a maximum amount of activity points that may be gained or earned over a predefined time period (e.g., at any one time, per day, per week, per month, per workout). In the illustrated example, the color used to display activity point portion 1011 may change to a first color upon a user reaching 50% of the target or threshold level of activity points. Activity point portion 1011 may further change to a second color upon the number of activity points reaching 75% of the target level and yet another color upon reaching 100% of the target level. Various thresholds for modifying the appearance of activity point portion 1011 may be defined depending on user preferences, system default settings, activity point provider/sponsor specifications and/or combinations thereof.

FIG. 10C illustrates another example of an interface displaying activity points. In interface 1020, activity points may be monitored using a graphical icon 1021 resembling, in the illustrated example, a battery gage. As a user earns activity points, the battery gage may begin filling up. The color of the battery gage contents may change depending on the current fill level of the battery gage. For example, the battery gage contents may be displayed in red when the fill level is at or below 25%, yellow when the fill level is above 25% and below 75% and green when equal to or above 75%. When the battery gage is entirely filled, the gage contents may change to yet another color such as blue or black. Alternatively, sections of the battery gage may be displayed in different colors. That is, a portion between 0% and 25% may be displayed in red while a portion between 25% and 50% may be displayed in yellow. Other types of representation may be used to display the level of activity points achieved or earned. For example, a user's current level of activity points may be represented using a fuel gage (e.g., a fuel needle pointing between empty and full), a thermometer-type gage, a pie chart and the like.

Figure 11:
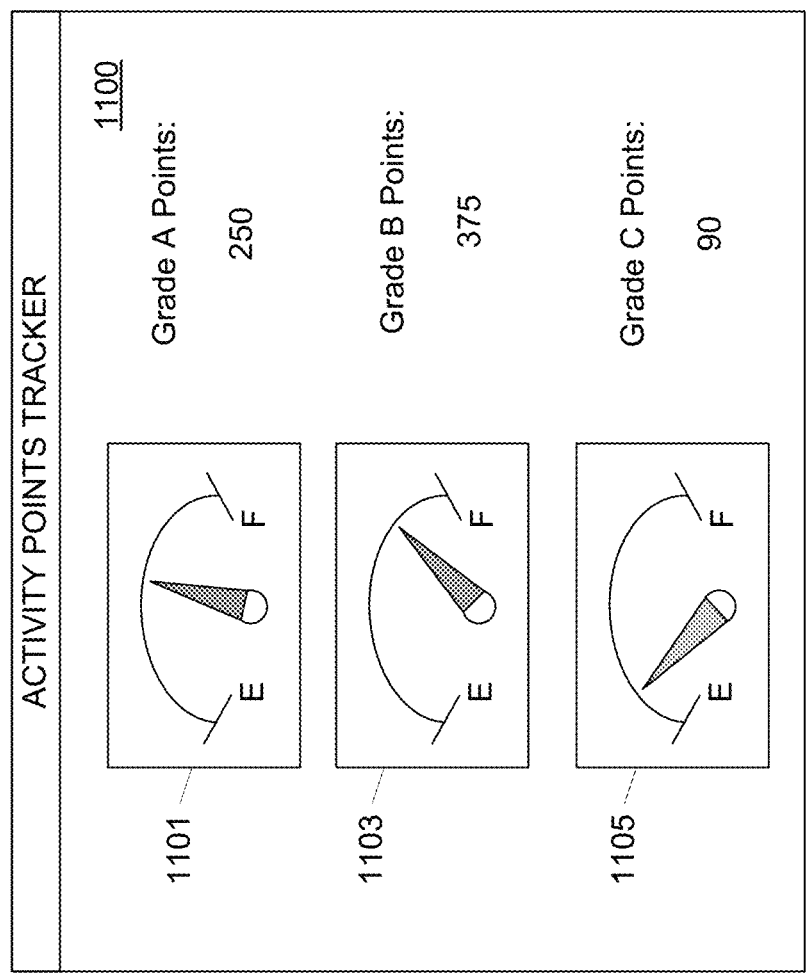
FIG. 11 illustrates an example user interface in which activity points are tracked using multiple gages according to one or more aspects described herein.

Different grades or types of fuel may be accumulated in different activity point pools. Accordingly, when a user wishes to review the amount of activity points earned, an interface may be generated where multiple activity point gages may be displayed. For example, FIG. 11 illustrates a user interface 1100 in which gage 1101 is configured to track activity points earned through certified devices, gage 1103 is configured to track and display activity points earned through non-certified devices and gage 1105 is configured to track and display activity points earned through all other sources (e.g., from manually entered information). Although gages 1101-1105 are illustrated in FIG. 11 using the same type of gage, gages 1101-1105 may comprise multiple different types of gages. Additionally or alternatively, the contents of gages 1101-1105 may be displayed in different colors to represent that different grades of activity points earned. For example, a pointer/needle of gage 1101 may be displayed in green while a pointer/needle of gage 1103 may be displayed in yellow. A pointer/needle in gage 1105 may be displayed in a third color such as red. In another example, a portion of the gage to the left of a pointer/needle of gage 1101 may be displayed in one color while the portion of the gage to the right of the pointer/need may be displayed in a second color. The portion to the left and the first color may represent the accumulated activity points. In gages 1103 and 1105, the portions to the left of their respective pointer/needles may be displayed in different colors (e.g., different from the color used in gage 1101) to represent the different grades.

In some arrangements, activity points of different grades or value may be tracked and visually represented in a single activity point gage. However, to allow a user to differentiate between the grades (and/or the modes through which the activity points were earned), the contents of an activity point gage may be displayed in different colors in accordance with a proportion of activity point grades. The accumulated activity points of any particular grade may be merged into a single continuous portion of the gage or may be allocated in the gage according to a time at which the points were earned. Hovering, clicking or otherwise interacting with a gage, e.g., gage 1105 of FIG. 11 may cause information and details about the activity points and/or athletic activity performed to be displayed. For example, referring again to FIG. 11, detailed information bubble 1107 may provide information regarding the number and types of workouts performed. Additionally, a total exercise or workout time may also be displayed.

Activity points and activity related information may also be displayed in one or more widgets or applications. For example, a user may display widgets on his or her FACEBOOK widget that receive athletic activity information from an athletic activity performance monitoring service. The widget may provide live feeds of such information or may retrieve activity data on a predefined schedule. Alternatively, a user may manually request updating of the activity data. In additional or alternative arrangements, applications or widgets may be downloaded to a user device (e.g., other than an athletic activity performance monitoring device), so that the user may view his or her athletic activity or other activity information without accessing a remote network site or using an athletic performance monitoring device. As discussed herein, the widgets or applications may be developed by third party developers and require access to proprietary protocols or interfaces.

Activity Data Tracking, Conversion and Storage

Wearable and non-wearable mobile devices such as athletic performance monitoring device 201 (FIG. 2) and watch 10 (FIGS. 7A and 7B) may be configured to measure athletic performance information for a variety of athletic activity types and to determine an amount of activity points earned through those activity types. For example, athletic performance monitoring device 201 may include a pedometer to measure a number of steps taken during walking or running exercises and an accelerometer to measure speed during such workouts. In another example, and as discussed above, a device such as watch 10 may connect (either wirelessly or through a wire) to various wearable and non-wearable sensors such as heart-rate sensors and accelerometers. The athletic measurements recorded for each of the multiple types of activity may be converted into activity points and summed to allow a user to measure his or her athletic performance across multiple types of activities. The mobile devices may store conversion rates for each type of athletic activity. If a conversion rate for a particular type of activity is not known, a default conversion rate may be used instead. Mobile devices may comprise consumer electronic devices such as watches, athletic bands, location determination devices, digital music players and the like.

Athletic performance monitoring devices may be configured specifically for one or more types of athletic activity or may provide generic tracking and monitoring for a variety of different athletic activity types. In the latter instance, one example of a generic performance monitoring device may be one that converts all movement to a number of steps taken (e.g., using a pedometer). Accordingly, regardless of whether the user is running, playing soccer, playing tennis or jumping rope, the athletic activity measure may register in steps. Accordingly, the number of athletic activity points earned through the use of such a generic monitoring device may use a step-based conversion rate. In another example, an athletic performance monitoring device may be configured to detect measures of athletic activity that are specific to a particular sport or athletic activity. For example, a monitoring device specifically configured for running may include sensors and/or software that provide running pace detection at which a user is running as well as a distance run. The running specific monitoring device may further be configured to use pace and distance information in determining a number of activity points corresponding to a running workout. In another example, a monitoring device may be configured to monitor and track soccer-related activities. Accordingly, the monitoring device may include sensors for detecting contact between a user and a ball and/or a force of impact between a user's foot and the ball for example. A conversion algorithm may then be used that incorporates such soccer-specific information in determining a number of activity points earned in a soccer workout. Other types of sports of athletic activities such as basketball, football, cycling, using gym equipment and the like may also have activity-specific measures. In addition to activity specific components and/or detection algorithms, athletic performance monitoring devices may also include generic detection systems so that the devices may be used in a wide variety of activities. For example, each of the above soccer athletic performance monitoring device and running performance monitoring device may include a general pedometer for detecting activity during non-soccer and non-running type activities, respectively.

Devices might also be configured to be sport-specific by defining a subset of athletic activity measures that may be monitored. For example, in a football configuration, the device may be configured to only measure heart rate and pace. In another example where the monitoring device is configured for soccer, the device might be configured to only monitor speed and foot-ball impact force. Additionally or alternatively, the type and content of feedback including motivational messages and coaching provided to the user may be sport-specific or selected based on the sport for which the monitoring device is configured. Accordingly, different messages may be provided to users depending on the sport for which the device is configured. In one example, the device is configured for soccer, a message such as "BEND IT LIKE BECKHAM!" might be displayed, whereas if the device is configured for swimming, such a message might not be provided to the user. Instead, for swimming, a message such as "CUT THROUGH THE WATER!" may be provided.

Moreover, by configuring a device for a particular sport, a trainer or coach may be able to push information to users based on sport. Accordingly, a trainer may develop or provide workouts that are intended for athletes in a particular sport. In such instances, the trainer may transmit the workout data to only those devices that are configured for the relevant sport or sports. In another example, a coach may transmit training profiles to each of the members of a team for a specific sport. Similarly, challenges, goals and other objectives may also be defined and transmitted in a sport-specific manner. In some arrangements, a device configured for a particular sport may ignore or discard data that is not intended for the particular sport.

Alternatively or additionally, devices may be classified into multiple categories such as certified and non-certified devices. These classifications may be defined by an entity or organization that provides user athletic activity performance monitoring service and/or that sponsors activity point rewards. The classifications may further affect the amount or grade of activity points earned. For example, data recorded by certified devices may be treated differently from data recorded by non-certified devices. As a more specific example, activity points earned through certified devices may be considered more valuable or reliable than activity points earned through manual entry or non-certified devices. Accordingly, a user may earn 1.5 points for every 10 minutes run when measured by a certified device in contrast to 1 point for every 10 minutes run for workouts recorded using a non-certified device. Device certification may be performed by one or more authorized entities, such as an entity that provides the athletic activity point currency and access to the products and/or services that may be exchanged therewith.

Certification may include insuring that the devices include adequate security components or software for preventing the falsification of athletic activity information (e.g., calories burned, miles run, steps taken) and corresponding activity points. According to one or more aspects, certification may be enforced by storing model and/or serial numbers of certified devices in a certification database. When a system wishes to determine whether a device is a certified device, the system may query the certification database with a model or serial number of the device. Alternatively or additionally, certified devices may include specific hardware and/or software components that are recognizable to another system or device. For example, an activity point conversion program running on a mobile device may be digitally signed by a certifying authority. Accordingly, when a user wishes to transmit or receive data to or from another device, the digital signature of the certifying authority may be transmitted to the other device for verification of certification.

In one or more arrangements, software, algorithms, product labels and/or services may be licensed to other companies for the creation of certified devices, software and/or hardware. Accordingly, third party companies or developers may create applications or add-on hardware that utilizes the activity performance monitoring features provided by an athletic activity performance monitoring and tracking service. For example, a third party developer may use application protocol interfaces (APIs) of a device to access activity tracking capabilities and information. The information may then be incorporated into third party software, such as a video game in which progression is measured by the user's athletic performance. In another example, a developer may create a mobile application that helps select music based on a current pace at which a user is running or walking, a number of steps taken, a number of calories burned, a rate at which a user is burning calories and the like. Accordingly, the mobile application may use device or application specific interfaces to access the necessary athletic activity information. The APIs and/or other tools that may be used by third party developers may include security mechanism to prevent unauthorized access to athletic activity information.

Alternatively or additionally, athletic performance data including, for example, miles run, calories burned, activity points earned and the like, may be transmitted between athletic performance monitoring devices such as device 201 and/or a remote athletic monitoring system. The transfer of data between devices may be performed through wired or wireless connections and networks including infrared connections, BLUETOOTH connections, wired and wireless local area networks, cellular networks, wide area networks such as the Internet and the like. The transmission of athletic information including activity points among performance monitoring devices, athletic activity data monitoring and tracking systems, non-athletic activity monitoring devices and other systems may be encrypted and/or transmitted using a secure or proprietary protocol to prevent unauthorized interception, access and/or tampering of such data. For example, Pretty Good Privacy (PGP) encryption may be used to encrypt athletic activity information. In another example, data may be transmitted using Secure Socket Layer (SSL) protocol to insure security. If the data is not encrypted according to an agreed-upon encryption algorithm or transmitted using a specified transmission protocol, the data may be rejected or communications in general may be denied.

Transmission and sharing of athletic activity information including activity points may allow a user to use multiple different athletic activity performance monitoring devices and/or other devices (e.g., personal computers, netbooks, mobile phones). For example, if a user uses different types of monitoring devices for different types of athletic activity, the user may wish to track an overall athletic activity level across all workouts and devices. Accordingly, the information collected and/or determined through each of the multiple devices may be shared and synchronized. However, in some configurations, activity point synchronization may require authorization through an activity point service to insure that activity points are not falsified, duplicated or modified in an unauthorized manner. For example, a user may be required to upload activity data to an activity point service from a first device and subsequently synchronize that data to each of one or more other devices the user owns through the activity point service. The activity point service may insure the legitimacy of synchronization between devices using such a configuration.

Figure 12:
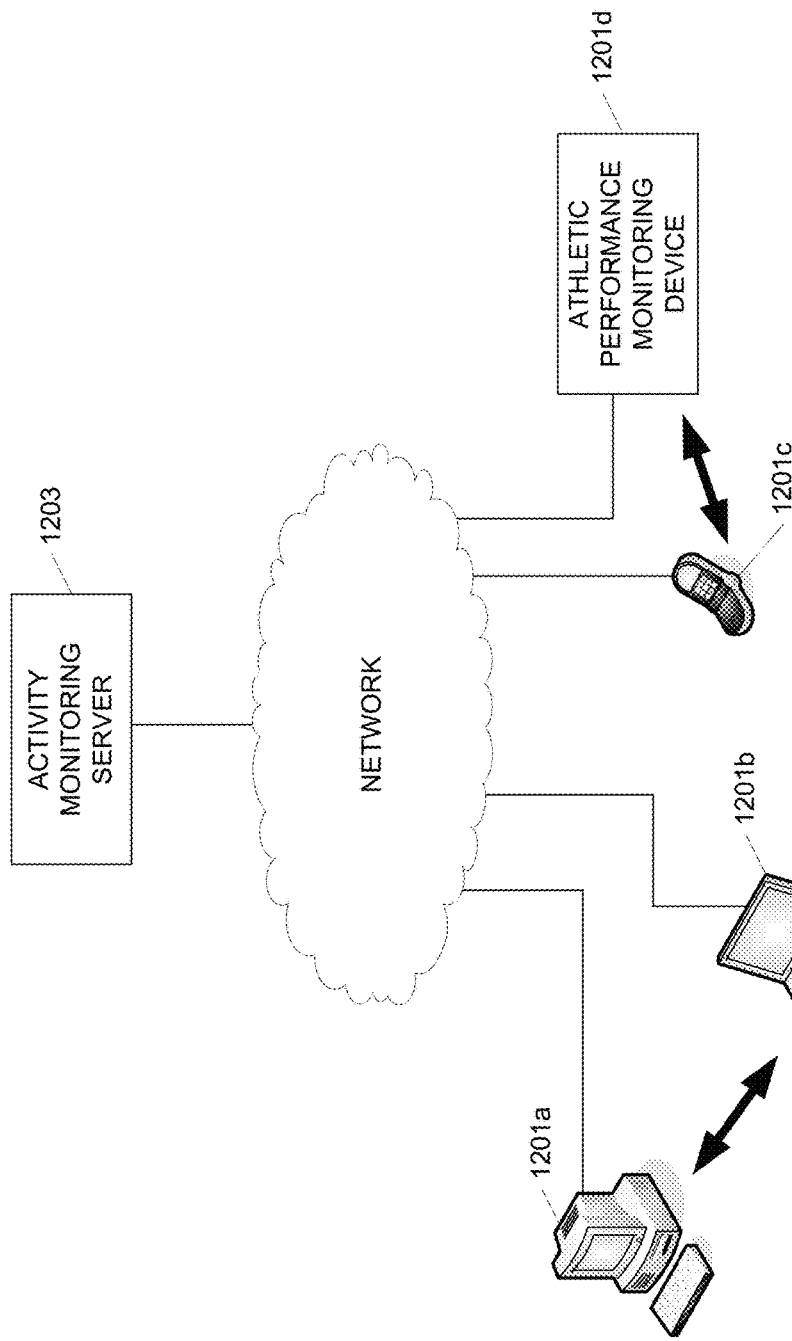
FIG. 12 illustrates an example synchronization environment in which activity data may be synchronized across multiple devices according to one or more aspects described herein.

FIG. 12 illustrates an example synchronization environment in which athletic activity information including performance data and activity points may be synchronized among devices 1201 through activity monitoring server 1203. Devices 1201 may include a personal computer 1201a, a laptop computer 1201b, a mobile telecommunications device 1201c and an athletic performance monitoring device 1201d. In particular, athletic activity data from each of the devices 1201 may be uploaded to monitoring server 1203 and subsequently downloaded and synchronized with each of devices 1201. Alternatively or additionally, devices 1201 may synchronize amongst each other without involvement of server 1203, e.g., between devices 1201a and 1201b or devices 1201c and 1201d. However, results from synchronization without involvement of server 1203 may be considered unofficial. Synchronization with monitoring server 1203 might still be required to use any earned activity points or achieve other types of recognition for recorded athletic activity performance data (e.g., earning of virtual trophies, winning a competition or challenge, fundraising).

In addition to athletic activities, a mobile device such as a performance monitoring device may monitor and track other types of activities such as a user's reading habits, shopping trends, browsing behavior, gaming interests, event participation history and the like. For example, mobile devices may include network communication capabilities that allow users to access a network such as the Internet. Accordingly, a user may use a mobile device not only to track and store athletic activity data but also to conduct on-line shopping, read articles, sign-up for events, play games, chat with other users and the like. The mobile device may thus be configured to record a history of the user's behavior such as shopping history, browsing history, gaming history, friends list, event participation history and the like. This information may be used to award the user with additional activity points and/or to customize a user's experience as described herein. For example, if a user purchases a pair of shoes, the shoe company may sponsor the award of 10 points for every dollar spent. In another example, if a user participates in a sponsored event, the sponsor may provide 100 activity points. In still another example, selecting and viewing advertisements may reward the user with 20 activity points per advertisement. Thus, activity points may be earned by the user for many of the non-athletic activities the user performs.

Data for other users might also be collected for a current user. For example, if a user wishes to track the athletic performance of a friend, the user may use his or her monitoring device to download or receive data for the friend. Such a process may require approval by the other user. This information, e.g., the type of information of the friend that the user views may also be used in determining user preferences, recommendations, suggestion; and/or customizing user experiences. For example, a user may frequently view details of a friend's soccer activities but not the friend's running workouts. In such an instance, a monitoring system may determine that the user is interested in soccer and less interested in running.

According to other aspects, a user's operation of a data collection and/or monitoring device such as device 201 (FIG. 2) or watch 10 (FIGS. 7A and 7B) may be monitored and tracked. For example, the number of times a user presses a button or activates a function on the device may be tracked. Such information may be used by an athletic activity monitoring and tracking service to determine preferences by a user including activity preferences, data display preferences (e.g., a user may prefer to display split times versus overall times or heart rate rather than calories burned), storage preferences (e.g., users may consistently and/or frequently delete workout data that is more than a week old) and the like. Based on this information, a service or system may customize various aspects of the activity monitoring and tracking service. In one example, the service may limit displays of historical workout data to the past week if the service determines that users frequently delete workout data more than a week old from their monitoring device. In another example, the service may provide offers for products, services, events and the like that correspond to walking activities if the service detects that the user frequently uses a pedometer function of a device such as watch 10 of FIGS. 7A and 7B. Other information that may be tracked based on usage of a device include preferred time of day or week for activities, preferred display configurations (e.g., split display versus whole displays), preferred information to be tracked (e.g., activity points versus calories burned) and the like.

The athletic and non-athletic activity data monitored and collected by a service may be used for a variety of purposes including the awarding and deducting of activity points. In one example, the data may be used to generate recommendations and/or suggestions for products, services, events, communities, articles and the like. In one example, a device may determine that the user has been exercising with the same pair of shoes for over 6 months. Accordingly, a system may recommend purchasing a new pair of shoes given the age of the current pair. The system may further recommend specific pairs of shoes or types of shoes based on the user's needs and/or preferences. For example, if sensors in a user's shoe indicate that the user has a pronation, the system may recommend shoes that are designed to correct for such a condition. In another example, if a new device that is an upgrade of a user's current device is available, the system may recommend or suggest purchasing the new device based on knowledge of the type of device the user currently uses. Alternatively or additionally, recommendations for a new device may be made based on the features most frequently or recently used by the user.

Additional information may also be gleaned from the collected data including a health status of a user. For example, heart conditions, high or low blood pressure, stress levels, overall physical condition and the like may be determined based on heart rate measurements, pace information, calories burned, distance run and the like. Additionally or alternatively, one or more portions of the collected data may be used to determine an overall athleticism score (e.g., SPARQ score).

In one or more arrangements, an activity monitoring and tracking service system may be used to configure monitoring devices such as monitoring device 201 (FIG. 2) and watch 10 (FIGS. 7A and 7B). For example, a user may logon to a website or activate an application that allows a user to customize a look and feel of the user interface displayed on the monitoring device, types of information to be monitored, tracked and/or stored, user information including preferences and the like. In one or more arrangements, the information may be stored as a device profile and may be replicated to other devices. Accordingly, a user may configure multiple devices by propagating or copying the profile (e.g., if a user has different devices for different sports or if a user decides to upgrade from a first device to a second device). To customize the interface of the monitoring device, the application or website may replicate the device's interface to provide the user with a visual indication of the selections and changes being made. The application or website may further allow a user to define different interface options for different modes of the device (e.g., a clock mode versus a stopwatch mode). According to another aspect, the user may also customize the behavior of various buttons and functions of the device. Thus, a user may customize the actions performed by the device in response to pressing of a particular device button using the application or website.

Devices such as athletic performance monitoring device 201 of FIG. 2 and watch 10 of FIGS. 7A and 7B may include various components for providing the features described herein. For example, changes in color and lighting may be affected using various types of lighting technology including light emitting diodes (LEDs), organic LEDs (OLEDs), liquid crystal displays (LCDs), e-ink or other electrowetting technologies, electroluminescence and the like. Additionally, wired and wireless communication components may be used to enable configuration and personalization of a device (for example, from another device), update firmware, receiving data from multiple sensors (e.g., biometric and environmental) and for detecting the presence of and sharing information among other devices.

Activity Information Submission

As noted herein, activity points may be sponsored by an entity. For example, an athletic product company may sponsor a website or service that allows users to track and monitor their athletic activity. In addition, the athletic activity may be used to earn activity points as a type of currency that may be spent on a variety of events, services, privileges (e.g., VIP access) and products. Accordingly, users may need to submit athletic activity information to an athletic activity monitoring service before being awarded a corresponding number of activity points and being allowed to spend those points on rewards. While an estimate of a number of activity points earned or accumulated may be provided to a user on a mobile athletic performance monitoring device in real-time, the athletic performance information or other activity information may still need to be submitted to the monitoring service for final confirmation and validation.

Figure 13:
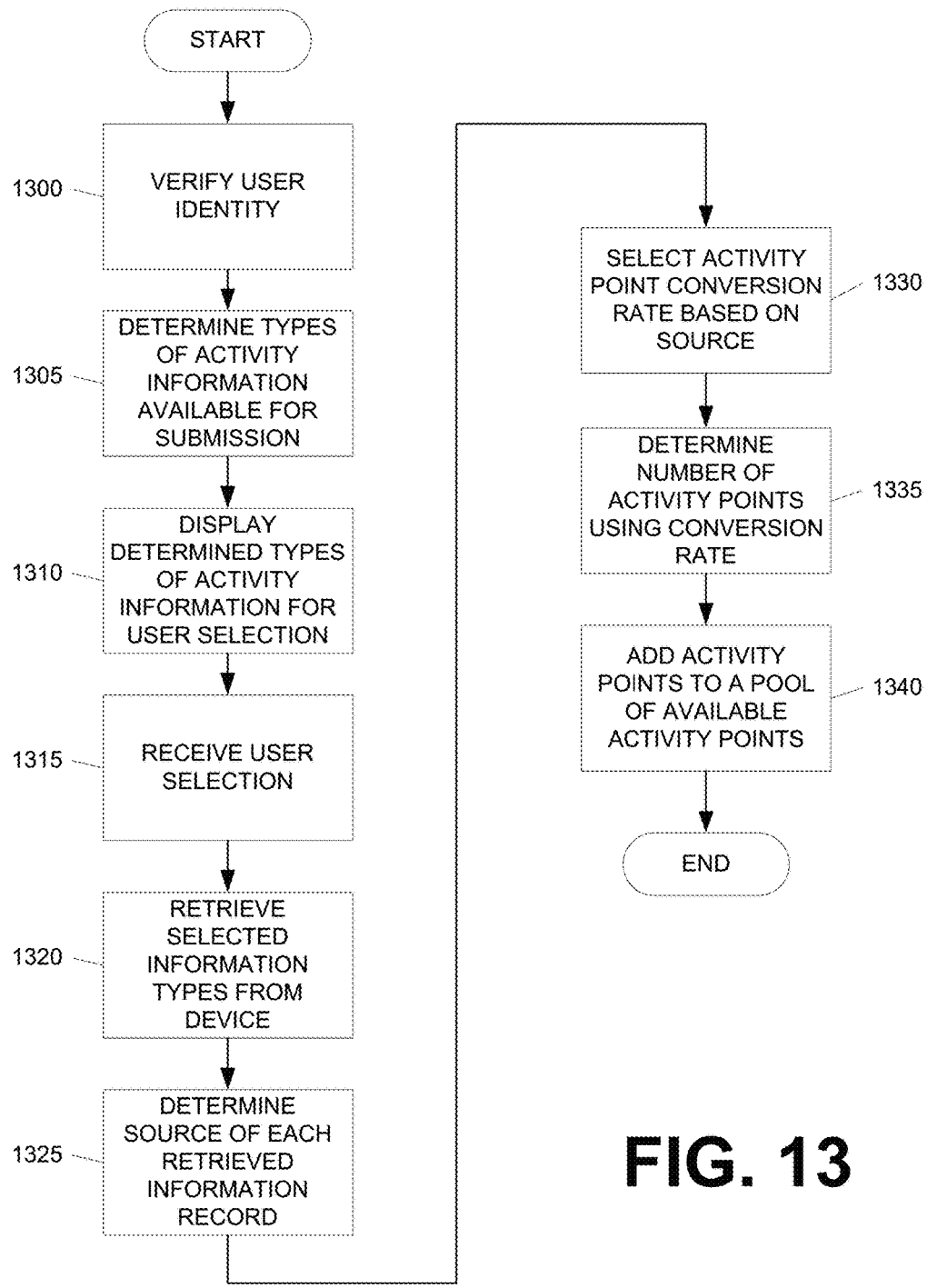
FIG. 13 illustrates an example method by which activity information may be submitted to an activity performance monitoring system and converted into activity points according to one or more aspects described herein.

FIG. 13 illustrates an example method by which activity information may be submitted to an activity monitoring service and converted into a number of activity points. Submission of activity information such as athletic activity performance data, shopping history, browsing history and the like may require an initial verification of a user's identity as shown in step 1300. For example, a user may be asked to enter login credentials such as a username and a password. Once the user has been verified, the system may, in step 1305, determine the types of activity information available (e.g., stored) in a device from which activity information is being submitted. For example, the system may submit a query to the device requesting identification of the various types of information stored thereon. In step 1310, the system may display the available types of activity information stored in the device for user selection. In some instances, a user might not wish to upload or submit all activity information stored on a device. Accordingly, the system may provide an opportunity for the user to select a subset of the information by only submitting certain types of activity information such as athletic workout information or shopping history data. Activity information may be categorized according to activity type, specific athletic or non-athletic activities (e.g., specific sports, shopping, advertisements, etc.), date and/or combinations thereof.

In step 1315, the system may receive a user selection of one or more of the types of activity information stored in the device. In step 1320, the system may retrieve the selected information from the device. The data may be stored in record format such that each workout or activity session comprises a single record. The record may include information such as an activity type, activity duration, athletic activity measures, other activity measures such as amount spent, a source of the information (e.g., user-entered, certified device, non-certified device), etc. Moreover, the retrieval of the data may be performed using a secure communication protocol such as SSL. Additionally or alternatively, the data may be encrypted prior to transmission to the retrieving system.

In step 1325, the system may determine a source of each activity information record retrieved from the device. For example, the system may determine whether information of a first activity information record was collected by a certified device or a non-certified device. Alternatively or additionally, the system may determine whether the information was manually entered by a user. This source identification information may be specified in each activity information record and extracted therefrom during the determination of step 1325 for example. In another example, identifying the information source may include determining whether the information stored in an information record is encrypted according to a digital signature indicative of a certified device. In yet another example, the system may determine a source of the activity information based on a model and/or serial number of a collecting device stored in each activity information record.

In step 1330, the system may select an activity point conversion rate for each activity information record based on the identified source of the activity information stored in each record. As discussed above, a first conversion rate may be provided for activity information collected by a certified device, a second conversion rate may be used for activity information collected by a non-certified device and a third conversion rate may be used for manually entered activity information. For example, the conversion rate for the activity information collected by the certified device may be higher than the conversion rate for activity information collected by non-certified devices. The conversion rate may also be selected based on the type or types of activity corresponding to the retrieved activity information. Selection of a conversion rate or algorithm may also depend on the types of activity information collected. For example, an information record may specify that the collected information corresponds to a running activity. However, if pace information was not collected, a conversion rate that takes pace into account might not be used. Instead, a conversion rate using distance, time and/or heart rate may be selected for converting the running activity performance data into activity points. Once a conversation rate has been selected, a number of activity points earned may be determined using the selected conversion rate and the relevant retrieved activity information in step 1335. The conversion algorithm may also specify the grade or type of activity points resulting from the conversion. For example, the grade of activity points earned using a certified device may be higher than the grade of activity points earned based on user-entered activity information. In step 1340, the system may add the determined number of activity points to a total number of activity points available to the user including, for example, all unspent activity points earned by the user. Further, different grades of activity points may be added to different activity point pools.

In one or more arrangements, a user may manually enter and submit activity information directly to an activity monitoring service or site. For example, a user may specify an amount of money spent on purchases, a number of miles run, a walking or running pace, an average heart rate, a number of calories burned, an amount of weight lifted, a number of repetitions performed and the like. The athletic monitoring service might restrict the number of activity entries a user may manually submit and/or a magnitude of those activity entries. Such restrictions may allow the system to prevent abuse of the self-entry feature. In one example, the system might only allow the user to enter 2 activity records per day or per week. Additionally or alternatively, the system might only allow the user to enter activity records that are less than a predefined activity measure threshold. For example, a user might not be allowed to enter an activity record that reflects purchases of more than $200. In another example, a user might not be allowed to manually enter information for a workout session that includes more than 5 miles run and/or 600 calories burned. Moreover, a system may require that manual entries are verified by one or more other users.

In one or more arrangements, submission of athletic activity information including activity points, activity data over time, device analytics, biometrics and the like may involve a filtering or normalization process. For example, a monitoring or tracking service may require information to be submitted using certain units of measure. In another example, the service might only allow certain types or amounts of information to be submitted, in which case the other types or remaining amount of information may be filtered by the submitting device or by the service system. In the case where there is a limit to the amount of information that may be provided, filtering may retain the most recent information while discarding older data. Alternatively, filtering may be performed in accordance with some other algorithm, which, in some cases, may take into account user preferences.

Figure 14:
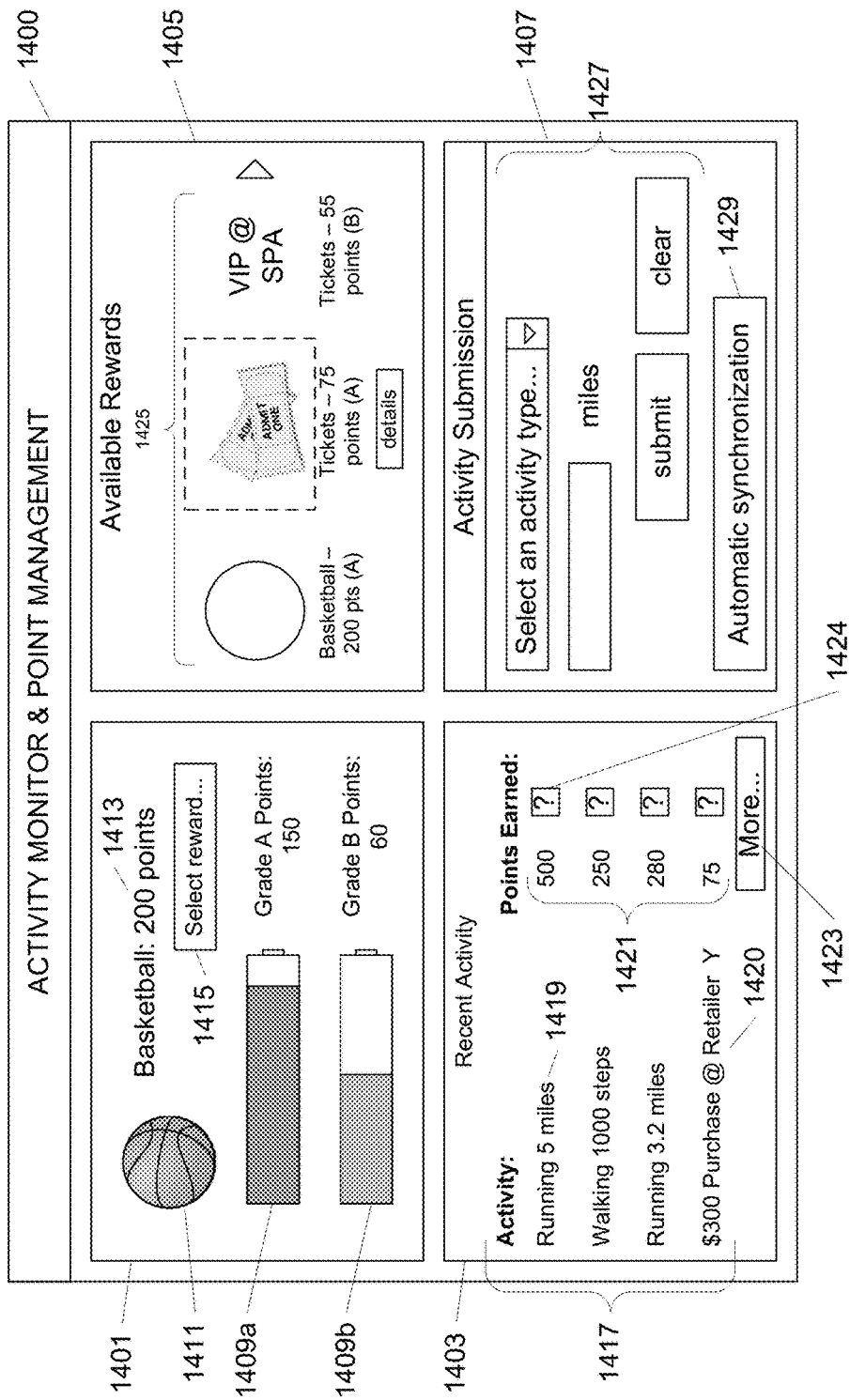
FIG. 14 illustrates an example interface in which accumulated activity points, activity information and activity information submission options may be displayed according to one or more aspects described herein.

FIG. 14 illustrates an example interface in which a user's accumulated activity points, activity information and activity information submission options may be displayed and accessed. Interface 1400 may be divided into multiple portions 1401, 1403, 1405 and 1407, each displaying various activity information and activity information options. For example, portion 1401 may include a display of a total number of activity points accumulated by and available to the user. As illustrated, portion 1401 may include gages 1409a and 1409b corresponding to different grades of activity points. Similar to differences in currency, the activity points represented in gage 1409a may be more valuable than the activity points represented in gage 1409b. According to one or more aspects, portion 1401 of interface 1400 may further display a goal 1411 and a number of points 1413 needed to achieve goal 1411. A user may be able to modify goal 1411 may selecting option 1415 and manually specifying a goal or choosing a new goal from a menu (not shown). In portion 1403, interface 1400 may display a recent activity listing 1417 of activities performed and submitted by the user. Activity record 1417 may include workout information such as running entry 1419. Alternatively, activity record 1417 may include other activity information such as most recent shopping event 1420, a number of advertisements reviewed (not shown), an article read (not shown) and the like. Additionally, activity record 1417 may display a number of activity points 1421 earned from each of the listed activities. Additional history option 1423 may further be provided in portion 1403, allowing the user to view other activities submitted, but not currently shown in portion 1403. Furthermore, each activity entry may include an option 1424 that allows the user to view detailed information relating to that activity. For example, the detailed information may include a breakdown of the activity point calculation, heart rate information for a run, a breakdown of purchases made at a retailer and the like.

Portion 1405 may display reward information and allow a user to browse various rewards that are achievable through the use of activity points. For example, portion 1405 may include a scrollable listing 1425 of rewards that may be purchased. Rewards that are within a user's available point range may be displayed in a first manner (e.g., in color and/or with visual details) while rewards that are not obtainable based on a user's currently available number of points may be displayed in a second manner (e.g., in an outline form, in black & white, grayed out, faded, etc.). The rewards 1425 displayed in portion 1405 may be selected in a variety of ways including based on a user's interests. A user's interests may be determined based on a history of user activity including types of workouts, products or services purchased, events attended, services subscribed to/purchased and the like. Upon selecting one of the rewards in listing 1425, the user may be provided with a details option to view additional information about the reward as well as a purchase option (if the user has sufficient points).

Portion 1407 may include an activity information submission region. The user may select between manual entry 1427 and automatic synchronization 1429. As noted above, manual entry 1427 may be performed through an interface in which a user may specify the type of activity performed and define various metrics associated therewith. In one or more arrangements, the metrics to be entered may be automatically selected based on the type of activity specified by the user. Alternatively, the user may select automated synchronization option 1429, where the system may detect activity information stored in one or more monitoring devices and upload that information. The user may be able to select a subset of less than all information available on the monitoring devices. Once the activity information has been submitted, one or more of portions 1401-1405 may be automatically updated based on the new information.

Activity Point Management

Figure 15:
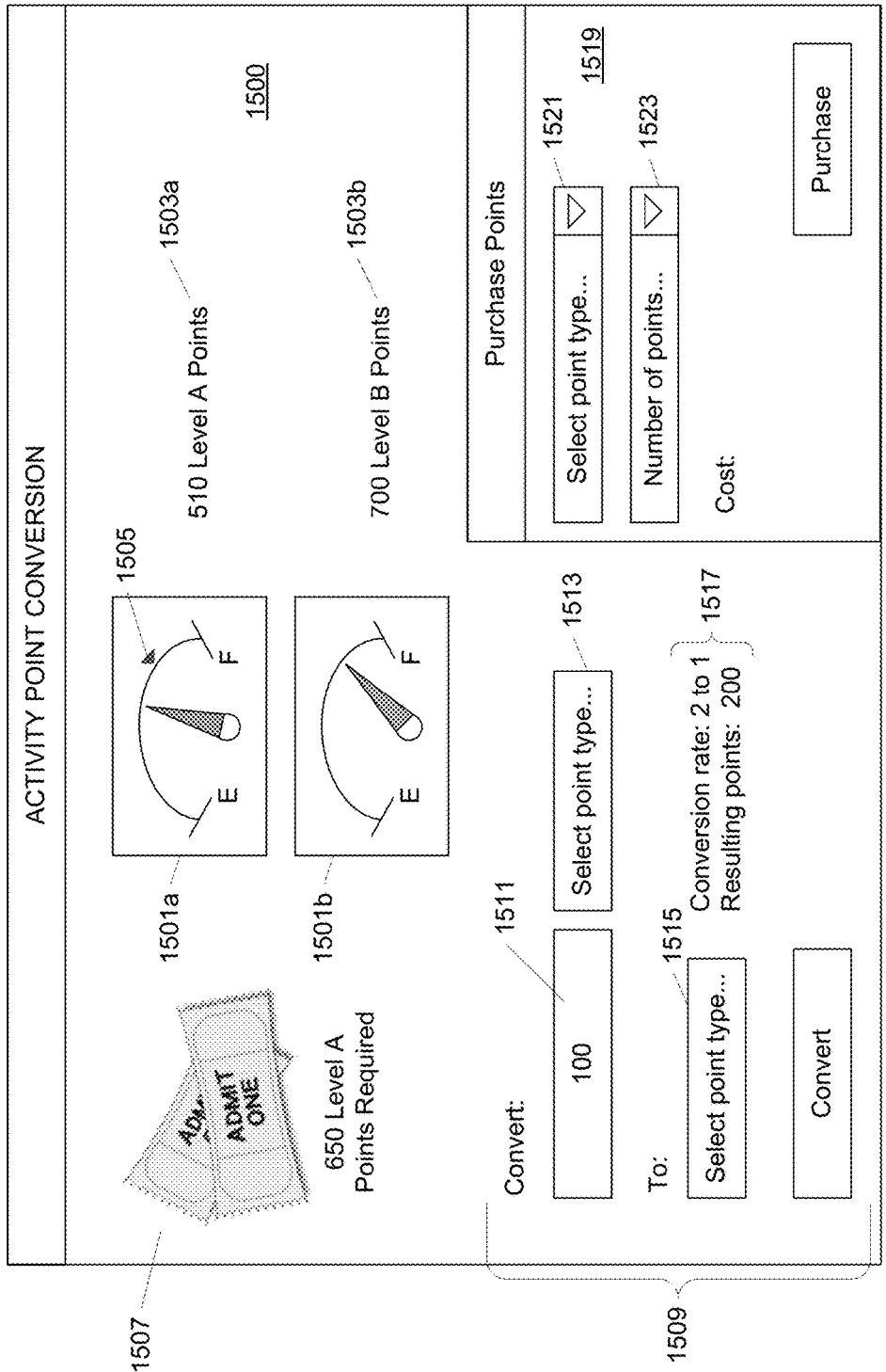
FIG. 15 illustrates an example user interface of a performance monitoring site in which multiple activity point gages are displayed to reflect the amount of activity points earned or available for each particular point type or grade.

A user may view and manage activity points in a variety of manners. For example, if multiple grades or types of activity points exist, different gages may be displayed for each of the multiple grades or types as described herein. FIG. 15 illustrates an example user interface 1500 of a performance monitoring site in which multiple activity point gages 1501 are displayed to reflect the amount of activity points earned or available for each particular point type or grade. A numeric value 1503 corresponding to the amount of activity points available may be displayed within each of gages 1501 as well. In one or more arrangements, the numeric value might only be displayed upon the user hovering over or otherwise interacting with gages 1501. In other arrangements, the numeric value might always be displayed. Additionally or alternatively, gages 1501 may include a point threshold indicator 1505 to allow a user to visually identify when a number of points has been accumulated. The point threshold indicator 1505 may correspond to a number of points needed for a reward, a number of points needed for an achievement, points needed for a video game and the like. In one example, threshold indicator 1505 may be displayed in a position corresponding to a number of points needed for a reward currently selected by a user (e.g., reward 1507).

Furthermore, selecting or otherwise interacting with one of gages 1501 may cause a pop-up window or other type of display to be displayed. The pop-up window may include detailed information relating to the selected gage. For example, the display may include grade information, conversion rates for various types of activity, a transaction history (e.g., points spent, points earned, how the points were spent, how the points were earned, etc.). The transaction history may provide a lifetime listing of activity submissions, activity point accumulating events, activity point consumption events and the like. Alternatively, the user may select a transactional history time period, rather than displaying a lifetime's worth of information. The pop-up window may further allow the user to reconfigure the appearance of the selected gage. For example, the user may select a new type of gage to use (e.g., thermometer, fuel gage, battery gage) and/or the color of the gage and/or contents thereof, change the size of the gage, modify a capacity of the gage and the like. For example, a user may modify the capacity of the gage by setting a new activity point goal or selecting a new reward goal. Additionally or alternatively, a user may be permitted to name the gage for easier identification. Further, a detailed view of the gages 1501 may include a breakdown of the types of activities contributing to the accumulated points in each gage. The breakdown may be displayed as a numerical list (e.g., by percentage or points) or may be visually represented by different colored sections of the gage. For example, a red portion of the gage may represent an amount of activity points earned through shopping, while a yellow portion of the gage may represent an amount of activity point earned through running workouts and a blue portion of the gage represents an amount of activity points earned through walking.

Interface 1500 may further include conversion options 1509 allowing a user to exchange activity points of one grade with activity points of another grade. For example, a user may enter a number of points in field 1511 and select a point grade in menu 1513 to convert. The user may then select a destination grade or desired grade of points in menu 1515. An information display 1517 may be provided to provide an indication of a number of points of the desired grade that will result from the conversion. Additionally, a conversion rate may be displayed in information display 1517. Furthermore, limits may be set on the number of points that may be exchanged for any one grade over a specified period of time (e.g., a day, a week, a month). The system may also restrict the types of conversions that are allowed. For example, points of grade 1 might only be convertible into points of lower grades, but not into points of higher grades. In another example where points of a particular grade might only be earned through certain types of activities, points of one grade might only be convertible into points of another grade that may also be earned through the same or similar activities. Various conversion rates may be instituted for the various types of points grades.

According to another aspect, activity points may be converted or used to determine an amount of athletic activity performed. For example, if workout information is conveyed from an athletic performance monitor device or other data collection system in activity points rather than in calories or miles, the system may translate the activity points into calories or some other measure of athletic activity. The translated information may be used to determine an activity level of the user, for example, or to determine whether a user has met an athletic activity goal, achieved an objective, or completed or won a challenge. In other examples, activity points may be converted into a number of steps, an average heart rate, a distance run, an average pace run or walked, a finishing position in a competition and the like.

Interface 1500 may further allow a user to manage activity points by purchasing or selling activity points. For example, option bar 1519 may allow a user to purchase additional activity points if the user would like to purchase a reward immediately but does not have a sufficient number of points (or a sufficient number points of a particular grade). The user may select a desired point grade using menu 1521 and a number of points desired from drop down menu 1523. Options provided in menu 1523 may change depending on the point grade selected using menu 1521. For example, a service may implement different limits for different grades of points so a maximum number of points purchaseable for higher point grades is lower than a maximum number of points purchaseable for lower point grades. Limits may be on a per day basis, per week, per month, per year and the like. Additionally or alternatively, the cost of points may be different depending on the point grades. Accordingly, higher value point grades may cost more than lower value point grades. Furthermore, the costs of one or more grades of activity points may become lower if a user's athletic activity level improved. Conversely, if a user's athletic activity declines or is low, the cost of activity points may be higher or may be increased. Other attributes and/or characteristics of a user may also affect the cost of activity points such as a number of athletic events in which the user has participated, a number of friends recruited to use the service and/or an athletic activity level trend.

Activity Point Consumption

Activity points may be consumed or recognized in a variety of manners. As noted above, users may spend activity points on a variety of items including services such as VIP treatment at stores, events, flights, hotels and other venues; product and/or service discounts (e.g., coupons or free products); video game related items including game credits (e.g., to buy additional weapons or levels), in-game powers or skills, or players (e.g., unlocking a famous athlete); and the like. The activity point cost of these items may be defined by the athletic performance monitoring service and may fluctuate depending on popularity. For example, activity points may be used to purchase flights or concert tickets. In one or more arrangements, a user may select one or more particular interests. Those interests may then be used to modify activity point costs of items relating to those interests. For example, if a user enjoys spa treatments, the user may be offered discounted services from spa treatments. A user may be restricted to a predefined number of interests that are reflected in the price of rewards. Alternatively or additionally, various services, products or other rewards may be discounted if a user allows advertisements to be displayed in his or her athletic performance monitoring site and/or if the user views a certain number of advertisements over a specified time period. For example, a user may allow the placement of advertisements in various locations of the user's site. Accordingly, the sponsors of those advertisements may offer discounts to that user for rewards that they provide through the athletic performance monitoring service. Alternatively, the athletic performance monitoring service may provide discounts based on advertisement revenue received from sponsors when users visit a specified number of advertisements.

Figure 16:
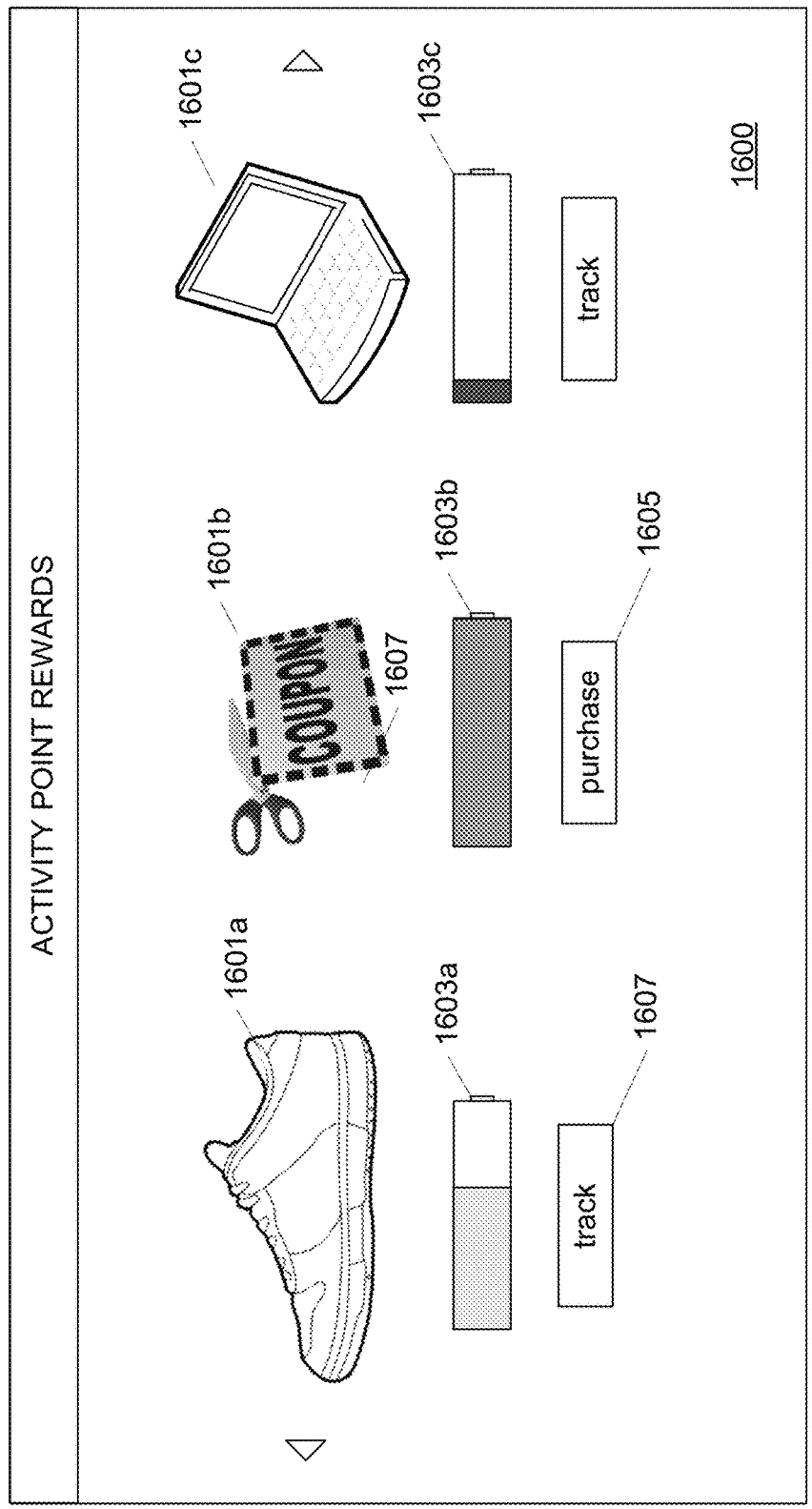
FIG. 16 illustrates an example reward browsing and selection user interface according to one or more aspects described herein.

FIG. 16 illustrates an example user interface 1600 configured to display multiple rewards that may be offered to a user. Rewards may be displayed in various manners depending on whether the user has a sufficient number of activity points to obtain the reward. For example, a user might not have sufficient activity points to purchase a shoe reward 1601a. Accordingly, shoe reward 1601a and computer reward 1601c may be displayed as an outline (e.g., without details). In another example, a user may have sufficient points to purchase a $25 coupon to a restaurant, in which case coupon reward 1601b may be displayed with detail and/or color. Additionally, interface 1600 may display a point tracker below each of rewards 1601. Point tracker 1603b, for example, may visually represent a progress a user has made toward earning a number of activity points needed to purchase corresponding reward 1601b. Similarly, point tracker 1603a may visually represent how many more points a user needs to be able to purchase reward 1601a. If a user has earned enough points for a reward, (e.g., reward 1601b), a purchase option 1605 may be displayed beneath the reward to facilitate the purchasing of that product. Moreover, a track option 1607 may be provided below one or more rewards such as reward 1601 to allow a user to use reward 1601 and an activity point cost thereof as a goal on a user's athletic performance monitoring site, a mobile athletic performance monitoring device and/or other mobile devices or computing systems. For example, upon selecting track option 1607, point tracker 1603a or a variation thereof (e.g., using a different type of tracker such as a fuel gage) may be displayed on a user's main athletic performance monitoring page.

Activity points may be consumed or spent in additional or alternative ways. For example, a user may wish to donate points to one or more charities or other organizations, events, services and the like. The donations may be tax-deductible based on an equivalent monetary value. Additionally or alternatively, a user may transfer or sell activity points to other users. For example, a user may gift a certain number of points to another user. A user may be required to pay a premium or other cost for transferring points to another user whereas a lower or no premium or cost may be associated with making donations to charitable organizations. If a user decides to sell his or her activity points, the service may further charge the user a percentage of the sales price, a listing fee or other transaction fee, sales tax and/or other added costs for the transaction. Limits may also be set by the service for the number of points that may be transferred between users, sold and/or donated. The limits may be defined in a dollar amount or by number of activity points. Limits may also be different depending on the type of transfer. For example, transfers between users may be limited to a first threshold (e.g., 500 points per month) while donations to charitable organizations may be unlimited. Points for sale, on the other hand, may be capped at 1000 points per week. Limits may also vary depending on the user. For example, users may subscribe to a premium service that allows higher or unlimited caps to points sold or transferred for free to other users. In another example, users with higher activity levels may be allowed higher limits for such transactions.

Achievements & Recognition

According to one or more arrangements, activity points may be earned by reaching predefined goals, completing events, reaching an objective, receiving a gift from others and the like. Goals may correspond to an objective defined for a limited amount of time. For example, a user may be invited to participate in a challenge where the first individual to finish 5 miles in under 45 minutes will receive a prize of 300 activity points. A second place prize in the amount of 150 points may be awarded as well. Such a competition or challenge may be sponsored by an organization such as the athletic performance monitoring service or may be a user defined event using the sponsoring user's own points. In another example, a first user may set a goal or objective for a second user and motivate the second user with an activity point prize. In yet another example, an athletic performance monitoring service may provide certain milestones that provide a user with an activity point aware upon reaching the milestone. Milestones or achievements may include satisfaction or reaching of thresholds or conditions without time limitations (for reaching the milestones or achievements).

Milestones may include running your first 5K race, completing a mile run in under 7 minutes, running 5 different routes, winning a race and the like. Non-athletic activity achievements might also be rewarded. For example, if a user purchases $100 worth of merchandise from a particular retailer, that retailer may reward the user with 5 activity points.

Non-activity point recognition may also be awarded based on a user's activity. For example, a user may earn badges that may be displayed on the user's public athletic performance monitoring page. In one particular example, a user may earn a virtual badge indicating that the user has maintained a specified level of fitness for a year or some other predefined time period. In another example, a badge may be awarded for exercising a certain number of consecutive days, months, weeks, etc. In yet another example, a physical reward such as a trophy, wristband, medal and the like may be rewarded for the achievement. Recognition might also include a title or special colors that are awarded to the user for a limited amount of time. A title may include "Superstar" or "Super Athlete" while special colors may include colors that are not ordinarily available for use in a customized home page or for clothing on a user's avatar. As with points, recognition may be removed from a user if the user's behavior is considered detrimental to physical fitness or athletic activity. For example, a user may be stripped of a "Superstar" title for eating more 500% more calories than burned in 1 week. In another example, if a user fails to complete an objective, challenge or goal, the user may also lose recognition.

Other rewards including those discussed herein might also be given to a user without requiring the consumption of activity points. For example, if a user reaches a significant milestone or accomplishes a goal, the prize or reward may be VIP treatment at an event. Accordingly, a user's activity might be rewarded not only by a corresponding number of activity points but also with products that would otherwise cost a specified number of activity points. In one example, if a user exceeds a personal best (e.g., time for running a mile), the user may be awarded with activity points and/or other types of recognition.

Challenges, Objectives and Goals

Activity points may also be awarded and deducted based on challenges, objectives and goals. For example, if a user completes an objective or goal, a number of activity points may be awarded. In another example, different numbers of activity points may be awarded for a challenge depending on a user's finish in the challenge. As noted herein, points might also be deducted if a user fails to complete a challenge, objective or goal. Challenges, objectives and goals may be generated by the user or issued by others including other athletes or coaches. In one or more arrangements, the user may explore and participate in various challenges by browsing through a challenge marketplace or community. Invitations may also be sent through social networking sites such as FACEBOOK and using information feed services such as TWITTER. Users may be able to check on the status of a challenge by viewing a live leaderboard that indicates a current progress of each of the challenge's participants. In some arrangements, the users may be able to view the progress or leaderboard through their monitoring devices or another device such as a personal computer. Alternatively or additionally, updates to challenge progress or status may be pushed to a user's device automatically.

Challenges, objectives and goals may also be suggested or recommended to the user by an athletic activity monitoring system. For example, the system may identify or generate challenges configured push a user to achieve a 10% gain in maximum distance run in one workout. Accordingly, the challenge may be defined using activity data collected from the user (in particular, a maximum distance run in a single workout). Challenges might also be selected or generated based on a user's known interests, characteristics and preferences. In one example, a user's athleticism rating (e.g., SPARQ rating) may be used to select or generate appropriate challenges for a user.

According to one or more aspects, an athletic activity monitoring device such as device 201 (FIG. 2) or watch 10 (FIGS. 7A and 7B) may include a display that visually reflects a state of the user's progress relative to a challenge, goal or objective. In one example, the display may change colors depending on the current position of the user in a challenge. If the user is in first place, for instance, the display may have a green background. If, however, the user is in second place, the display may have a black or yellow background. Alternatively or additionally, other visual characteristics may be modified to represent different levels of progress including blinking or flashing text, images or backgrounds, moving text or images, different icons and the like. Updates to the user's status in the challenge may be automatically received from a challenge monitoring service system. A user may also manually refresh the status. A user may further elect to advertise or publish status information on a social network or community site for friends and other users to track his or her progress.

CONCLUSION

Providing an activity environment having one or more of the features described herein provides a user with an immersive experience that will encourage and motivate the user to engage in athletic activities and improve his or her fitness. By providing the user with current that may be used to purchase real world items that may be unrelated to fitness or athletic activity, the user is further motivated to engage in those activities that reward additional currency. Users may further communicate through social communities and challenge one another to reach various levels of fitness. In addition to traditional athletic activity measures, the use of an activity currency allows users to view their fitness level and activity in a more practical manner.

What is claimed is:

1. A non-transitory computer readable medium storing computer executable instructions that, when executed by a processor, cause the processor to at least to perform:
   automatically receive, via a wireless network, an item identifier of an athletic item from a portable electronic device of a user upon the item identifier being received at the portable electronic device from a passive radio frequency transmitter that is configured to transmit the item identifier to the portable electronic device when the portable electronic device is positioned proximate to the passive radio frequency transmitter;
   determine that the athletic item is a certified item, the determination comprising:
      compare the item identifier to a certification database comprising a plurality of identifiers of certified items; and
      determine that the item identifier matches one of the plurality of identifiers of certified items;
   based on determining that the athletic item is a certified item, transmit a first sport-related content related to the athletic item to the portable electronic device;

output for display, on at least a portion of a display of the portable electronic device, the first sport-related content;

receive, at an engageable interface element of the portable electronic device, a user identifier identifying the user of the certified item;

obtain encrypted usage information relating to interactions by the user with the athletic item based on the user identifier, wherein at least a portion of the encrypted usage information is obtained from a second device configured to detect interactions by the user with the athletic item;

determine, based on the encrypted usage information, that the second device is a certified device;

based on the determining that the second device is a certified device, convert the encrypted usage information from the second device to an activity unit at a first conversion rate;

based on determining that the athletic item is a certified item and determining that the activity unit meets a threshold requirement, automatically transmit a second sport-related content related to the athletic item to the portable electronic device; and output for display, on at least a portion of a display of the portable electronic device, the second sport-related content.

2. The non-transitory computer readable medium of claim 1, wherein the second sport-related content includes information related to one or more athletic events associated with the athletic item.

3. The non-transitory computer readable medium of claim 1, wherein the determining that the athletic item is a certified item is based on a digital signature of the encrypted usage information.

4. The non-transitory computer readable medium of claim 1, wherein at least one of the first sport-related content and the second sport-related content includes information about one or more athletic events associated with the athletic item.

5. The non-transitory computer readable medium of claim 4, wherein a first athletic event of the one or more athletic events occurs on a first date and a second athletic event of the one or more athletic events occurs on a second date,
wherein the athletic item comprises an article of sports apparel, and
wherein the encrypted usage information comprises information relating to the user using the article of sports apparel on the first date.

6. The non-transitory computer readable medium of claim 5, wherein the encrypted usage information further comprises information relating to the user using the article of sports apparel on the first date and the second date.

7. The non-transitory medium of claim 1, wherein the non-transitory computer readable medium further comprises computer-executable instructions that when executed by the processor perform at least:
prior to selecting transmitting the second sport-related content, selecting the second sport-related content is from a plurality of certified content offerings, based on usage of the athletic item.

8. The non-transitory computer readable medium of claim 1, wherein the non-transitory computer readable medium further comprises computer-executable instructions that when executed by the processor perform at least:
select the first conversion rate from a plurality of conversion rates based on the encrypted usage information regarding at least one of the second device and the athletic item.

9. The non-transitory computer readable medium of claim 8, wherein the first conversion rate is selected based on a source of the encrypted usage information.

10. The non-transitory computer readable medium of claim 1, wherein the non-transitory computer readable medium further comprises computer-executable instructions that when executed by the processor perform at least:
convert the encrypted usage information into an estimated amount of activity unit.

11. The non-transitory computer readable medium of claim 1, wherein the encrypted usage information comprises non-athletic activity information.

12. A method comprising:
automatically receiving an item identifier of an athletic item from a portable electronic device of a user, upon the item identifier being received at the portable electronic device from a passive radio frequency transmitter that is configured to transmit the item identifier to the portable electronic device when the portable electronic device is positioned proximate to the passive radio frequency transmitter;

determining that the athletic item is a certified item, the determination comprising:
comparing the item identifier to a certification database comprising a plurality of identifiers of certified items; and
determining that the item identifier matches one of the plurality of identifiers of certified items;

based on determining that the athletic item is a certified item, transmitting a first sport-related content related to the athletic item to the portable electronic device;

displaying, on at least a portion of a display of the portable electronic device, the first sport-related content;

obtain encrypted usage information relating to interactions by the user with the athletic item, wherein at least a portion of the encrypted usage information is obtained from a second device configured to detect interactions by the user with the athletic item;

determine, based the encrypted usage information, that the second device is a certified device;

based on the determining that the second device is a certified device, convert the encrypted usage information from the second device to an activity unit at a first conversion rate;

receiving, at an engageable interface element of the portable electronic device, a user identifier identifying the user of the certified item;

based on determining that the athletic item is a certified item, determining that the user identifier is valid, and determining that the activity unit meets a threshold requirement automatically transmitting a second sport-related content related to the athletic item to the portable electronic device; and displaying, on at least a portion of a display of the portable electronic device, the second sport-related content.

13. The method of claim 12, wherein the second sport-related content includes information related to one or more athletic events associated with the athletic item.

14. The method of claim 12, wherein the determining that the athletic item is the certified item is based on a digital: of the encrypted usage information.

15. A non-transitory computer readable medium storing computer executable instructions that, when executed by a processor, cause the processor to at least to perform:
automatically receive an item identifier of an athletic item from a portable electronic device of a user upon the item identifier being received at the portable electronic device from a passive radio frequency transmitter that is configured to transmit the item identifier to the portable electronic device when the portable electronic device is positioned proximate to the passive radio frequency transmitter;

determine that the athletic item is a certified item, the determination comprising:
　compare the item identifier to a certification database comprising a plurality of identifiers of certified items; and
　determine that the item identifier matches one of the plurality of identifiers of certified items;

based on determining that the athletic item is a certified item, transmit a first sport-related content related to the athletic item to the portable electronic device;

output for display, on at least a portion of a display of the portable electronic device, the first sport-related content;

receive, at an engageable interface element of the portable electronic device, a user identifier identifying the user of the certified item;

obtain encrypted usage information relating to interactions by the user with the athletic item based on the user identifier, the encrypted usage information comprising non-athletic activity, wherein at least a portion of the encrypted usage information is obtained from a second device configured to detect interactions by the user with the athletic item;

determine, based on the encrypted usage information, that the second device is a certified device;

based on the determining that the second device is a certified device, convert the encrypted usage information from the second device to an activity unit at a first conversion rate; and based on determining that the athletic item is a certified item, determining that the user identifier is valid, and determining properties of the encrypted usage information, automatically transmit a second sport-related content related to the athletic item to the user in a format that is viewable on the portable electronic device.

* * * * *

UNITED STATES PATENT AND TRADEMARK OFFICE
CERTIFICATE OF CORRECTION

PATENT NO. : 10,467,716 B2
APPLICATION NO. : 15/849042
DATED : November 5, 2019
INVENTOR(S) : Hoffman et al.

Page 1 of 1

It is certified that error appears in the above-identified patent and that said Letters Patent is hereby corrected as shown below:

In the Claims

Column 37, Claim 7, Line 52:
Before "medium", insert --computer readable--

Column 38, Claim 14, Line 60:
Delete "digital:¶" and insert --digital signature-- therefor Signed and Sealed this
Nineteenth Day of May, 2020

Andrei Iancu
*Director of the United States Patent and Trademark Office*